United States Patent
Baumgarth et al.

[11] Patent Number: 6,028,069
[45] Date of Patent: Feb. 22, 2000

[54] HETEROCYCLYL-CONDENSED BENZOYLGUANIDINES, THEIR PRODUCTION AND USE AS INHIBITORS OF THE CELLULAR NA+/H+-ANTIPORTER

[75] Inventors: Manfred Baumgarth, Darmstadt; Rolf Gericke, Seeheim; Klaus-Otto Minck, Ober-Ramstadt; Norbert Beier, Reinheim, all of Germany

[73] Assignee: Merck Patent Gesellschaft mit berschranker Haftung, Darmstadt, Germany

[21] Appl. No.: 09/091,652

[22] PCT Filed: Dec. 16, 1996

[86] PCT No.: PCT/EP96/05645
§ 371 Date: Mar. 30, 1999
§ 102(e) Date: Mar. 30, 1999

[87] PCT Pub. No.: WO97/23476
PCT Pub. Date: Jul. 3, 1997

[30] Foreign Application Priority Data

Dec. 23, 1995 [DE] Germany .................... 195 48 708

[51] Int. Cl.[7] .................. A61K 31/54; A61K 31/425; A61K 31/38; C07D 277/62; C07D 327/06
[52] U.S. Cl. .................. 514/227.5; 514/367; 514/432; 514/443; 514/439; 514/434; 544/59; 548/171; 549/28; 549/53; 549/32; 549/15; 549/23
[58] Field of Search .................. 549/28, 53, 32, 549/15, 23; 514/432, 443, 227.5, 439, 434, 436, 367; 544/59; 548/171

[56] References Cited

U.S. PATENT DOCUMENTS

| | | | |
|---|---|---|---|
| 5,627,194 | 5/1997 | Rakhit et al. | 514/315 |
| 5,712,304 | 1/1998 | Elbe et al. | 514/272.4 |
| 5,767,289 | 6/1998 | Nakamura et al. | 549/23 |
| 5,789,436 | 8/1998 | Kato et al. | 514/443 |
| 5,821,250 | 10/1998 | Wu et al. | 514/300 |
| 5,849,784 | 12/1998 | Bertenshaw et al. | 514/432 |
| 5,863,936 | 1/1999 | Gaeta et al. | 514/443 |
| 5,919,814 | 7/1999 | Guillaumet et al. | 514/432 |

FOREIGN PATENT DOCUMENTS

| | | |
|---|---|---|
| 416499 | 3/1991 | European Pat. Off. . |
| 589336 | 3/1994 | European Pat. Off. . |
| 590455 | 4/1994 | European Pat. Off. . |
| 622356 | 11/1994 | European Pat. Off. . |
| 639573 | 2/1995 | European Pat. Off. . |
| 659748 | 6/1995 | European Pat. Off. . |
| 676395 | 10/1995 | European Pat. Off. . |

OTHER PUBLICATIONS

Yamamoto et al, "Preparation and formulation of benzothiazine derivatives as NA + /H+ exchange inhibitors", CA 128:244058, 1998.

*Primary Examiner*—Deborah C. Lambkin
*Attorney, Agent, or Firm*—Millen, White, Zelano & Branigan

[57] ABSTRACT

Cyclic sulphones of formula (I) are disclosed, in which: $R^1$ and $R^2$ each independently of one another stand for H, A, $CF_3$, $CH_2F$, $CHF_2$, $C_2F_5$, Hal, OH, OA, $NH_2$, NHA, $NA_2$, $NO_2$ or CN; X stands for $CR^4R^5$, C=Z, O, S, NH, NA or $NR^3$; Y stands for $CR^6R^7$, C=Z, O, NH, NA, or $NR^3$; Z stands for O, S, NH, NA, NOH, NOA, $CH_2$, CHA or $CA_2$; $R^4$, $R^5$, $R^6$ and $R^7$ each independently of one another stand for H, A, $R^3$, Hal, OH, OA, SH, SA, $NH_2$, NHA or $NA_2$, or alternatively, $R^5$ and $R^6$ or $R^7$ and $R^8$ can together represent a bond, only one such bond being present in each molecule; $R^4$ and $R^5$ together can also stand for O—$(CH_2)_2$—O or O—$(CH_2)_3$—O; $R^8$ and $R^9$ each independently of one another stand for H or A; A stands for alkyl with 1–6 C atoms; Hal stands for F, Cl, Br or I; and $R^3$ stands for phenyl or benzyl which is unsubstituted or single-, double- or triple-substituted by A, OA, $NH_2$, NHA, $NA_2$, F, Cl, Br and/or $CF_3$; and n is 0 or 1. Also disclosed are the physiologically tolerable salts of these compounds. These compounds and their salts have anti-arrhythmic properties and act as inhibitors of the cellular Na+/H+-antiporter.

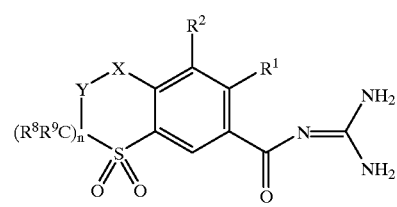

(I)

9 Claims, No Drawings

HETEROCYCLYL-CONDENSED BENZOYLGUANIDINES, THEIR PRODUCTION AND USE AS INHIBITORS OF THE CELLULAR NA+/H+-ANTIPORTER

This application is a 371 of PCT/EP96/05645 filed Dec. 16, 1996.

The invention relates to cyclic sulfones of the formula I

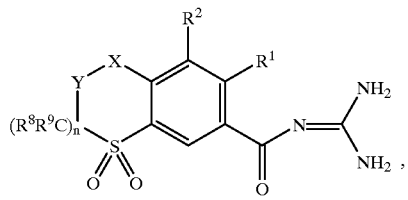

in which
$R^1$ and $R^2$ in each case independently of one another are H, A, $CF_3$, $CH_2F$, $CHF_2$, $C_2F_5$, Hal, OH, OA, $NH_2$, NHA, $NA_2$, $NO_2$ or CN,
X is $CR^4R^5$, C=Z, O, S, NH, NA or $NR^3$,
Y is $CR^6R^7$, C=Z, O, NH, NA or $NR^3$,
Z is O, S, NH, NA, NOH, NOA, $CH_2$, CHA or $CA_2$.
$R^4$, $R^5$, $R^6$ and $R^7$ in each case independently of one another are H, A, $R^3$, Hal, OH, OA, SH, SA, $NH_2$, NHA or $NA_2$ or else
$R^5$ and $R^6$ or $R^7$ and $R^8$ in each case together are also a bond, it being possible in each molecule for a maximum of only one bond of this type to occur;
$R^4$ and $R^5$ together are also O—$(CH_2)_2$—O or O—$(CH_2)_3$—O,
$R^8$ and $R^9$ in each case independently of one another are H or A,
A is alkyl having 1 to 6 C atoms,
Hal is F, Cl, Br or I and
$R^3$ is phenyl or benzyl which is unsubstituted or mono-, di- or trisubstituted by A, OA, $NH_2$, NHA, $NA_2$, F, Cl, Br and/or $CF_3$ and
n is 0 or 1,
and their physiologically acceptable salts.

The invention was based on the object of finding novel compounds having useful properties, in particular those which can be used for the production of medicaments.

It has been found that the compounds of the formula I and their physiologically acceptable salts have useful pharmacological properties together with good tolerability.

The novel compounds are inhibitors of the cellular $Na^+/H^+$ antiporter, i.e. active compounds which inhibit the $Na^+/H^+$ exchange mechanism of the cells (Düsing et al., Med. Klin. 87, 378–384 (1992)) and which are thus good antiarrhythmics which are particularly suitable for the treatment of arrhythmias which occur as a result of oxygen deficiency.

The best known active compound of the acylguanidines group is amiloride. However, this substance primarily shows a hypotensive and saluretic action, which is undesirable, in particular in the treatment of cardiac arrhythmias, while the antiarrhythmic properties are only very weakly pronounced. Benzoylguanidines are described, for example, in DE 44 04 183. The compounds described in the prior art, however, are structurally clearly different from those claimed here.

The invention relates to compounds of the formula I and their physiologically acceptable salts.

The substances according to the invention of the present application show a good cardioprotective action and are therefore particularly suitable for infarct treatment, infarct prophylaxis and for the treatment of angina pectoris. The substances furthermore counteract all pathological hypoxic and ischaemic damage so that the diseases caused primarily or secondarily thereby can be treated. The active compounds are likewise highly suitable for preventive applications.

On account of the protective actions of these substances in pathological, hypoxic or ischaemic situations, further application possibilities result in surgical interventions for the protection of temporarily undersupplied organs, in organ transplantations for the protection of the removed organs, in angioplastic vascular or cardiac interventions, in ischaemias of the nervous system, in the therapy of states of shock and for the preventive treatment of essential hypertension.

Furthermore, the compounds can also be employed as therapeutics in disorders caused by cell proliferation, such as arteriosclerosis, diabetic late complications, oncoses, fibrotic disorders, in particular of the lung, liver and kidneys, and organ hypertrophies and hyperplasias. Moreover, the substances are suitable for diagnostic application for the recognition of diseases which are accompanied by an increased activity of the $Na^+/H^+$-antiporter, e.g. in erythrocytes, platelets or leucocytes.

The actions of the compounds can be determined with the aid of methods known per se, such as are indicated, for example, by N. Escobales and J. Figueroa in J. Membrane Biol. 120, 41–49 (1991) or by L. Counillon, W. Scholz, H. J. Lang and J. Pouysségur in Mol. Pharmacol, 44, 1041–1045 (1993).

Suitable experimental animals are, for example, mice, rats, guinea-pigs, dogs, cats, monkeys or pigs.

The compounds can therefore be used as pharmaceutical active compounds in human and veterinary medicine. They can furthermore be used as intermediates for the preparation of other pharmaceutical active compounds.

In the formulae indicated, A is a branched or unbranched alkyl group having 1–6, preferably 1–4, in particular 1, 2 or 3 C atoms, specifically preferably methyl, additionally preferably ethyl, propyl, isopropyl, butyl, isobutyl, furthermore preferably sec-butyl, tert-butyl, pentyl, isopentyl (3-methylbutyl), hexyl or isohexyl (4-methylpentyl).

$R^1$ is preferably A, in particular methyl or ethyl, or hydrogen.

$R^2$ is preferably hydrogen, while $R^3$ is preferably phenyl or benzyl.

X and Y are in each case independently of one another particularly preferably —$CH_2$—, —$CH(CH_3)$—, —C(=$CH_2$)—, —$C(CH_3)_2$—, —CH(OH)—, —COH($CH_3$)—, —$C(OH)R^3$—, —$C(OCH_3)CH_3$—, —CH($OCH_3$)—, —$C(OCH_3)R_3$—, —CHCl—, —CH($NH_2$)—, —CH($NA_2$)—, —CH(CN)—, —CO—, —C(=NOH)—, —C(=NOA)—, —C(O—$CH_2$—$CH_2$—O)—, —S—, —O—, —NH—, —NA—, or else further also preferably X and Y together are —CH=CH—, —$C(CH_3)$=CH—, —CH=$C(CH_3)$—, =CH—$CH_2$—, =$C(CH_3)$—$CH_2$— or =CH—$CH(CH_3)$—.

$R^8$ and $R^9$ are preferably independently of one another H, methyl or ethyl.

$R^5$ and $R^6$ or $R^7$ and $R^8$, however, can also in each case together be a bond, where it is the case, however, that only one bond of this type can be present per molecule.

Hal is preferably F, Cl or Br.

It is generally the case that all radicals such as, for example, A, which can occur in the molecule several times, can be identical or different, i.e. independent of one another.

Accordingly, the invention relates in particular to those compounds of the formula I in which at least one of the radicals mentioned has one of the preferred meanings indicated above. Some preferred groups of compounds can be expressed by the formulae Ia to Ig below, which correspond to the formula I and in which the radicals not described in greater detail have the meaning indicated in the formula I, but in which in Ia X and Y are each CH$_2$ and n=0;
in Ib n=0 and X or Y is CH(CH$_3$) and the other radical in each case is CH$_2$;
in Ic X and Y together are —CH=CH—, —CH=C(CH$_3$)—, —C(CH$_3$)=CH—, —CH$_2$—C(=CH$_2$)—, —C(=CH$_2$)—CH$_2$—, —C(CH$_3$)$_2$—CH$_2$— or —CH$_2$—C(CH$_3$)$_2$— and n=0
in Id Y is CH$_2$ and X is CHOH, C(CH$_3$)OH, CR$_3$OH, CHOCH$_3$, CA(OCH$_3$), CR$^3$(OCH$_3$), CHCl, CH(NH$_2$), CH(NHA), CH(NA$_2$), CH(CN), C=O, C(O—CH$_2$CH$_2$—O), C(=NOH) or C(=NOA) and n=0;
in Ie X=O, n=0 and Y is CH$_2$, CH(CH$_3$) or C(CH$_3$)$_2$;
in If X=NH, NA or NR$_3$, Y is CH$_2$, CH(CH$_3$) or C(CH$_3$)$_2$ and n=0;
in Ig the unit —(CR$^8$R$^9$)$_n$—Y—X— is —CH$_2$—CH=CH— or —CH=CH—CH$_2$—.

Additionally, those compounds are particularly preferred which have the preferred meanings mentioned under Ia to If, but in which n=1 and —CR$^8$R$^9$— is preferably CH$_2$, CH(CH$_3$) or C(CH$_3$)$_2$.

The invention additionally relates to a process for the preparation of the compounds of the formula I according to claim 1, and of their salts, characterized in that a compound of the formula II

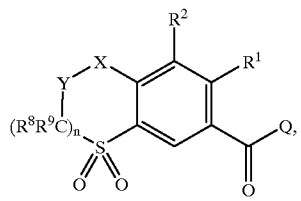

II in which R$^1$, R$^2$, R$^8$, R$^9$, X, Y and n have the meanings indicated previously and Q is Cl, Br, OA, O—CO—A, O—CO—Ph, OH or another reactive esterified OH group or easily nucleophilically substitutable leaving group, is reacted with guanidine,
or in that a compound otherwise corresponding to the formula I, but which instead of one or more hydrogen atoms contains one or more reducible groups and/or one or more additional C—C— and/or C—N bonds, is treated with a reducing agent,
or in that a compound otherwise corresponding to the formula I, but which instead of one or more hydrogen atoms contains one or more solvolysable groups, is treated with a solvolysing agent
and/or in that a base of the formula I which is obtained is converted into one of its salts by treating with an acid.

The compounds of the formula I are otherwise prepared by methods known per se, such as are described in the literature (e.g. in the standard works such as Houben-Weyl, Methoden der organischen Chemie [Methods of Organic Chemistry], Georg-Thieme-Verlag, Stuttgart; Organic Reactions, John Wiley & Sons, Inc., New York; and in the patent application indicated above), namely under reaction conditions which are known and suitable for the reactions mentioned. In this case, use can also be made of variants which are known per se, but not mentioned here in greater detail.

If desired, the starting substances can also be formed in situ in such a way that they are not isolated from the reaction mixture, but immediately reacted further to give the compounds of the formula I.

Preferably, compounds of the formula I are prepared by reacting an activated carboxylic acid derivative of the formula II, where Q is particularly preferably Cl or —O—CH$_3$, with guanidine. Particularly suitable reaction variants are also those in which the free carboxylic acid II (Q=OH) is reacted in a manner known per se to give the respective activated derivative and this is then reacted directly, without intermediate isolation, with guanidine. Methods in which an intermediate isolation is unnecessary are, for example, activation with carbonyldiimidazole, dicyclohexylcarbodiimide or the Mukayama variant (Angew. Chem. 91, 788–812 (1979)).

The carboxylic acids of the formula II and their derivatives used as intermediates can be prepared, for example, by (a) base-catalyzed intramolecular cyclization of 3-methylsulfonylbenzoic acids or derivatives thereof which in the 4-position carry a carbonyl or cyano group, e.g.

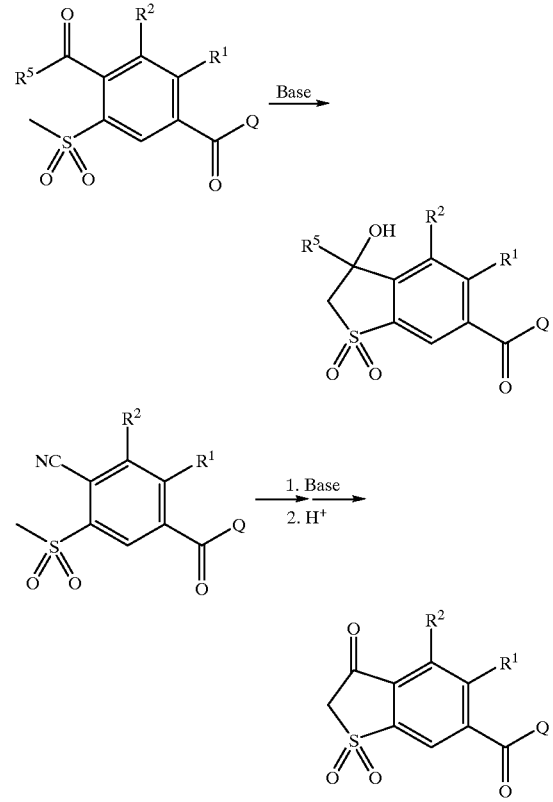

(b) Heck reaction of suitable 3-alkenylsulfonyl-4-bromobenzoic acid derivatives, e.g.

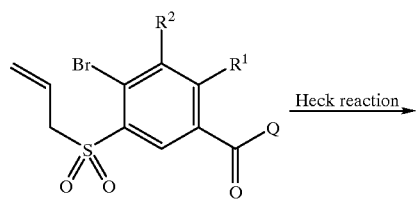

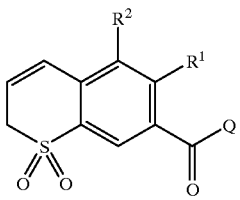

(for Heck reaction see, for example, Org. React. 27, 345 (1982))

(c) intramolecular nucleophilic substitution of 4-halobenzoic acids or their derivatives which in the 3-position carry a suitable hydroxyl, amino or mercaptoalkylsulfonyl radical (R), e.g.

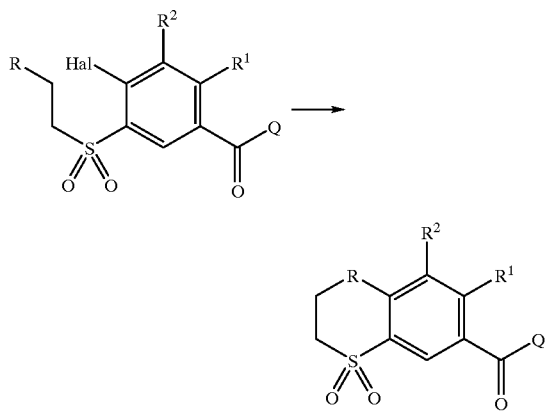

(d) oxidation of cyclic sulfides of the general formula

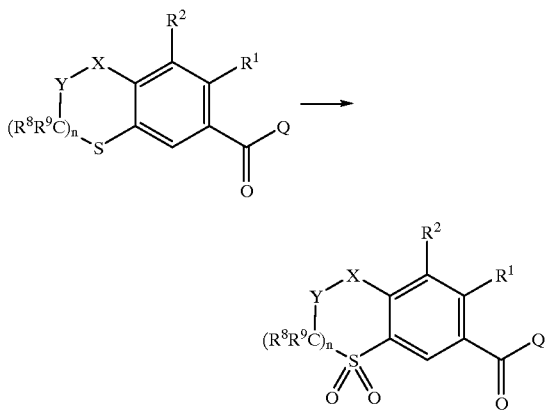

(e) addition of carbonyl compounds to mercaptophenols or -anilines and subsequent oxidation

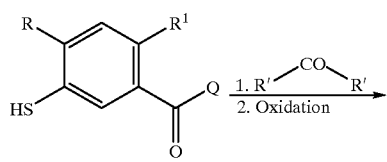

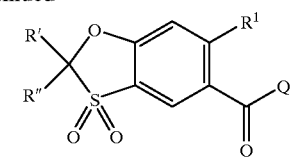

or

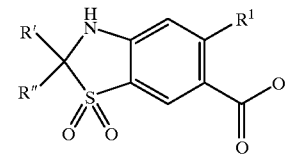

(R=OH or $NH_2$;
$R^1$ and Q as defined)

The reactions indicated are standard reactions of organic chemistry and are described, for example, in J. March, Adv. Org. Chemistry, 3rd. Ed., John Wiley & Sons (1985).

The cyclic sulfones thus obtained can be further derivatized or cyclized by customary methods.

The reaction of a reactive carboxylic acid derivative of the formula II with guanidine is carried out in a manner known per se, preferably in a protic or aprotic polar or non-polar inert organic solvent.

A preferred variant, however, also consists in reacting the reaction components with one another directly, without addition of a solvent.

In the preparation of II or in the reaction of II with guanidine, it is likewise expedient to work in the presence of a base or using an excess of the basic component. Suitable bases are preferably, for example, alkali metal or alkaline earth metal hydroxides, carbonates and alkoxides or organic bases such as triethylamine or pyridine, which are also used in an excess and then can simultaneously serve as solvents.

Suitable inert solvents are, in particular, alcohols such as methanol, ethanol, isopropanol, n-butanol or tert-butanol; ethers such as diethyl ether, diisopropyl ether, THF or dioxane, glycol ethers such as ethylene glycol monomethyl or monoethyl ether (methyl glycol or ethyl glycol), ethylene glycol dimethyl ether (diglyme); ketones such as acetone or butanone; nitriles such as acetonitrile; nitro compounds such as nitromethane or nitrobenzene; esters such as ethyl acetate; amides such as hexamethylphosphoramide; sulfoxides such as dimethyl sulfoxide (DMSO); chlorinated hydrocarbons such as dichloromethane, chloroform, trichloroethylene, 1,2-dichloroethane or carbon tetrachloride; hydrocarbons such as benzene, toluene or xylene. Mixtures of these solvents with one another are furthermore suitable.

Particularly suitable solvents are methanol, THF, dimethoxyethane, dioxane, water or mixtures which can be prepared therefrom. Suitable reaction temperatures are, for example, temperatures between 20° and the boiling point of the solvent. The reaction times are between 5 min and 12 h. It is expedient to employ an acid scavenger in the reaction. These include all types of bases which do not interfere with the reaction itself. However the use of inorganic bases such as potassium carbonate or of organic bases such as triethylamine or pyridine or else an excess of the guanidine is particularly suitable.

Furthermore, the compounds of the formula I can be obtained by liberating them from their functional derivatives by solvolysis, in particular hydrolysis, or by hydrogenolysis.

Preferred starting substances for the solvolysis or hydrogenolysis are those which otherwise correspond to the formula I, but instead of one or more free amino and/or hydroxyl groups contain corresponding protected amino and/or hydroxyl groups, preferably those which instead of an H atom which is bonded to an N atom carry an amino protective group, in particular those which instead of an HN group carry an R'—N group in which R' is an amino protective group, and/or those which instead of the H atom of a hydroxyl group carry a hydroxyl protective group, e.g. those which correspond to the formula I but which instead of an OH group carry an OR" group in which R" is a hydroxyl protective group.

There can also be two or more—identical or different—protected amino and/or hydroxyl groups in the molecule of the starting substance. If the protective groups present are different from one another, in many cases they can be removed selectively.

The expression "amino protective group" is generally known and relates to groups which are suitable for protecting (or blocking) an amino group from chemical reactions, but which are easily removable after the desired chemical reaction has been carried out at another position in the molecule. Typical groups of this type are particularly unsubstituted or substituted acyl, aryl (e.g. 2,4-dinitrophenyl (DNP)), aralkoxymethyl (e.g. benzyloxymethyl (BOM)) or aralkyl groups (e.g. benzyl, 4-nitrobenzyl, triphenylmethyl). As the amino protective groups are removed after the desired reaction (or reaction sequence), their nature and size is otherwise not critical; however those having 1–20, in particular 1–8 C atoms, are preferred. The expression "acyl group" is to be interpreted in the widest sense in connection with the present process. It includes acyl groups derived from aliphatic, araliphatic, aromatic or heterocyclic carboxylic acids or sulfonic acids, as well as, in particular, alkoxycarbonyl, aryloxycarbonyl and especially aralkoxycarbonyl groups. Examples of acyl groups of this type are alkanoyl such as acetyl, propionyl, butyryl; aralkanoyl such as phenylacetyl; aroyl such as benzoyl or toluoyl; aryloxyalkanoyl such as phenoxyacetyl; alkoxycarbonyl such as methoxycarbonyl; ethoxycarbonyl, 2,2,2-trichloroethoxycarbonyl, isoprop-oxycarbonyl, tert-butoxycarbonyl (BOC), 2-iodo-ethoxycarbonyl; aralkyloxy-carbonyl such as benzyloxycarbonyl (CBZ), 4-methoxybenzyloxycarbonyl, 9-fluorenylmethoxycarbonyl (FMOC). Preferred amino protective groups are BOC, DNP and BOM, and additionally CBZ, benzyl and acetyl.

The expression "hydroxyl protective group" is likewise generally known and relates to groups which are suitable for protecting a hydroxyl group from chemical reactions, but which are easily removable after the desired chemical reaction has been carried out at another position in the molecule. Typical groups of this type are the abovementioned unsubstituted or substituted aryl, aralkyl or acyl groups, and additionally also alkyl groups. The nature and size of the hydroxyl protective groups is not critical, as they are removed again after the desired chemical reaction or reaction sequence; groups having 1–20, in particular 1–10 C atoms, are preferred. Examples of hydroxyl protective groups are, inter alia, tert-butyl, benzyl, p-nitrobenzyl, p-toluenesulfonyl and acetyl, benzyl and acetyl being particularly preferred.

The functional derivatives of the compounds of the formula I to be used as starting substances can be prepared according to customary methods, such as are described, for example, in the standard works and patent applications mentioned, e.g. by reaction of compounds which correspond to the formulae II and III, but where at least one of these compounds contains a protective group instead of an H atom.

The liberation of the compounds I from their functional derivatives is carried out—depending on the protective group used—e.g. using strong acids, expediently using trifluoroacetic acid or perchloric acid, but also using other strong inorganic acids such as hydrochloric acid or sulfuric acid, strong organic carboxylic acids such as trichloroacetic acid or sulfonic acids such as benzene- or p-toluenesulfonic acid. The presence of an additional inert solvent is possible, but not always necessary.

Suitable inert solvents are preferably organic, for example carboxylic acids such as acetic acid, ethers such as tetrahydrofuran (THF) or dioxane, amides such as dimethylformamide (DMF), halogenated hydrocarbons such as dichloromethane, and additionally also alcohols such as methanol, ethanol or isopropanol as well as water. Additionally, mixtures of the abovementioned solvents are suitable. Trifluoroacetic acid is preferably used in an excess without addition of a further solvent, perchloric acid in the form of a mixture of acetic acid and 70% perchloric acid in the ratio 9:1. The reaction temperatures for the cleavage are expediently between approximately 0 and approximately 50°; the reaction is preferably carried out between 15 and 30° (room temperature).

The BOC group can preferably be removed, for example, using 40% trifluoroacetic acid in dichloromethane or using approximately 3 to 5 N HCl in dioxane at 15–60°, the FMOC group using an approximately 5–20% solution of dimethylamine, diethylamine or piperidine in DMF at 15–50°. Removal of the DNP group is also carried out, for example, using an approximately 3–10% solution of 2-mercaptoethanol in DMF/water at 15–30°.

Hydrogenolytically removable protective groups (e.g. BOM, CBZ or benzyl) can be removed, for example, by treating with hydrogen in the presence of a catalyst (e.g. of a noble metal catalyst such as palladium, expediently on a support such as carbon). Suitable solvents in this case are those indicated above, in particular, for example, alcohols such as methanol or ethanol or amides such as DMF. The hydrogenolysis is generally carried out at temperatures between approximately 0 and 100° and pressures between approximately 1 and 200 bar, preferably at 20–30° and 1–10 bar. Hydrogenolysis of the CBZ group takes place well, for example, on 5–10% Pd—C in methanol at 20–30°.

A base of the formula I can additionally be converted into the associated acid addition salt using an acid. For this reaction, suitable acids are those which give physiologically acceptable salts. Thus inorganic acids can be used, e.g. sulfuric acid, nitric acid, hydrohalic acids such as hydrochloric acid or hydrobromic acid, phosphoric acids such as orthophosphoric acid, sulfamic acid, and additionally organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids and laurylsulfuric acid.

The compounds of the formula I contain one or more chiral centres and can therefore exist in racemic or in optically active form. Racemates which are obtained can be separated into the enantiomers mechanically or chemically by methods known per se. Preferably, diastereomers are formed from the racemic mixture by reaction with an optically active resolving agent. Suitable resolving agents are, for example, optically active acids, such as the D- and L-forms of tartaric acid, diacetyltartaric acid, dibenzoyltartaric acid, mandelic acid, malic acid, lactic acid or the various optically active camphorsulfonic acids such as β-camphorsulfonic acid. Resolution of enantiomers with the aid of a column packed with an optically active resolving agent (e.g. dinitrobenzoylphenylglycine) is also advantageous.

Of course, it is also possible to obtain optically active compounds of the formula I by the methods described above by using starting substances (e.g. those of the formula II) which are already optically active.

The compounds of the formula I and their physiologically acceptable salts can be used for the production of pharmaceutical preparations, in particular in a non-chemical way. In this context, they can be brought into a suitable dose form together with at least one solid, liquid and/or semiliquid excipient or auxiliary and, if appropriate, in combination with one or more other active compounds.

The invention relates additionally to compositions, in particular pharmaceutical preparations, comprising at least one compound of the formula I and/or one of its physiologically acceptable salts.

These preparations can be used as medicaments in human or veterinary medicine. Suitable excipients are organic or inorganic substances which are suitable for enteral (e.g. oral) and parenteral administration or topical application and do not react with the novel compounds, for example water, vegetable oils, benzyl alcohols, polyethylene glycols, glycerol triacetate, gelatine, carbohydrates such as lactose or starch, magnesium stearate, talc, lanolin and petroleum jelly. In particular, tablets, coated tablets, capsules, syrups, juices or drops are used for oral administration, suppositories are used for rectal administration, solutions, preferably oily or aqueous solutions, and additionally suspensions, emulsions or implants are used for parenteral administration, ointments, creams, pastes, lotions, gels, sprays, foams, aerosols, solutions (e.g. solutions in alcohols such as ethanol or isopropanol, acetonitrile, DMF, dimethylacetamide, 1,2-propanediol or mixtures thereof with one another and/or with water) or powders are used for topical application. The novel compounds can also be lyophilized and the lyophilizates obtained used, for example, for the production of injection preparations.

In particular for topical application, liposomal preparations are also suitable. The preparations indicated can be sterilized and/or contain auxiliaries such as lubricants, preservatives, stabilizers and/or wetting agents, emulsifiers, salts for affecting the osmotic pressure, buffer substances, colorants, flavourings and/or aromatic substances. If desired, they can also contain one or more other active compounds, e.g. one or more vitamins.

The compounds of the formula I and their physiologically acceptable salts can be administered to humans or animals, in particular mammals such as monkeys, dogs, cats, rats or mice and are used in the therapeutic treatment of the human or animal body and in the control of diseases, in particular in the therapy and/or prophylaxis of disorders of the cardiovascular systems. They are therefore suitable for the treatment of arrhythmias, in particular if these are caused by oxygen deficiency, of angina pectoris, infarcts, ischaemias of the nervous system such as, for example, stroke or cerebral oedema, of states of shock and for preventive treatment.

The substances can additionally be employed as therapeutics in disorders in which cell proliferation plays a part, such as arteriosclerosis, diabetic late complications, oncoses, fibroses and organ hypertrophies and hyperplasias, in particular in disorders of the prostate.

In this case the substances according to the invention are generally administered in analogy to known antiarrhythmics, e.g. aprindine, preferably in doses between approximately 0.01 and 5 mg, in particular between 0.02 and 0.5 mg per dose unit. The daily dose is preferably between approximately 0.0001 and 0.1, in particular between 0.0003 and 0.01 mg/kg of body weight. The specific dose for each specific patient depends, however, on all sorts of factors, for example on the activity of the specific compound employed, on the age, body weight, general state of health, sex, on the diet, on the time and route of administration, on the excretion rate, pharmaceutical substance combination and severity of the particular disorder to which the therapy applies. Oral administration is preferred.

In the following examples "customary working up" means:

If necessary, water is added, the mixture is extracted with an organic solvent such as ethyl acetate, the organic phase is separated off, the organic phase is dried over sodium sulfate, filtered and evaporated, and the residue is purified by chromatography and/or crystallization.

EXAMPLE 1

1.9 g of sodium is introduced into 40 ml of dried methanol under a nitrogen atmosphere, with stirring and exclusion of moisture. The solution obtained is treated at room temperature with 8.7 g of guanidine hydrochloride and stirred for 30 minutes. The suspension is filtered, the filtrate is treated with 4 g of methyl 2,3-dihydro-3-hydroxy-1-benzothiophene-6-carboxylate-1,1-dioxide [obtainable by sodium methoxide cyclization and subsequent acid treatment of methyl 3-methylsulfonyl-4-cyanobenzoate and sodium borohydride reduction of the ketone obtained] and stirred at 50° for 3 hours. The reaction mixture is then treated with water with ice-cooling, saturated with sodium chloride and extracted with ethyl acetate. After customary working up, N-diaminomethylene-2,3-dihydro-3-hydroxy-1-benzothiophene-6-carboxamide-1,1-dioxide, m.p. 240–241°, is obtained. Treatment with methanesulfonic acid in methanol gives the corresponding methanesulfonate, m.p. 204–206°.

The following are obtained analogously
from methyl 2,3-dihydro-3-hydroxy-5-methyl-1-benzothiophene-6-carboxylate-1,1-dioxide
   N-diaminomethylene-2,3-dihydro-3-hydroxy-5-methyl-1-benzothiophene-6-carboxamide-1,1-dioxide, methanesulfonate: m.p. 266–267° (from methanol);
from methyl 2,3-dihydro-3-hydroxy-3,5-dimethyl-1-benzothiophene-6-carboxylate-1,1-dioxide
   N-diaminomethylene-2,3-dihydro-3-hydroxy-3,5-dimethyl-1-benzothiophene-6-carboxamide-1,1-dioxide, m.p. 243–245°, methanesulfonate: m.p. 214–216°;
from methyl 2,3-dihydro-3-hydroxy-3-ethyl-5-methyl-1-benzothiophene-6-carboxylate-1,1-dioxide [sic]
   N-diaminomethylene-2,3-dihydro-3-hydroxy-3-methyl-5-ethyl-1-benzothiophene-6-carboxamide-1,1-dioxide, m.p. 126–128°, methanesulfonate: 218–220°;
from methyl 2,3-dihydro-3-hydroxy-5-ethyl-1-benzothiophene-6-carboxylate-1,1-dioxide
   N-diaminomethylene-2,3-dihydro-3-hydroxy-5-ethyl-1-benzothiophene-6-carboxamide-1,1-dioxide;
from methyl 2,3-dihydro-3-hydroxy-2,2,5-trimethyl-1-benzothiophene-6-carboxylate-1,1-dioxide N-diaminomethylene-2,3-dihydro-3-hydroxy-2,2,5-trimethyl-1-benzothiophene-6-carboxamide-1,1-dioxide, m.p. 253°, methanesulfonate: 262–263°;

from methyl 2,3-dihydro-3-chloro-3-methyl-5-ethyl-1-benzothiophene-6-carboxylate-1,1-dioxide
N-diaminomethylene-2,3-dihydro-3-chloro-3-methyl-5-ethyl-1-benzothiophene-6-carboxamide-1,1-dioxide;

from methyl 2,3-dihydro-3-chloro-5-ethyl-1-benzothiophene-6-carboxylate-1,1-dioxide
N-diaminomethylene-2,3-dihydro-3-chloro-5-ethyl-1-benzothiophene-6-carboxamide-1,1-dioxide;

from methyl 2,3-dihydro-3-chloro-1-benzothiophene-6-carboxylate-1,1-dioxide
N-diaminomethylene-2,3-dihydro-3-chloro-1-benzothiophene-6-carboxamide-1,1-dioxide;

from methyl 2,3-dihydro-3-chloro-3-methyl-1-benzothiophene-6-carboxylate-1,1-dioxide
N-diaminomethylene-2,3-dihydro-3-chloro-3-methyl-1-benzothiophene-6-carboxamide-1,1-dioxide;

from methyl 2,3-dihydro-3-cyano-5-methyl-1-benzothiophene-6-carboxylate-1,1-dioxide
N-diaminomethylene-2,3-dihydro-3-cyano-5-methyl-1-benzothiophene-6-carboxamide-1,1-dioxide;

from methyl 2,3-dihydro-3-cyano-3-methyl-5-ethyl-1-benzothiophene-6-carboxylate-1,1-dioxide
N-diaminomethylene-2,3-dihydro-3-cyano-3-methyl-5-ethyl-1-benzothiophene-6-carboxamide-1,1-dioxide;

from methyl 2,3-dihydro-3-cyano-5-ethyl-1-benzothiophene-6-carboxylate-1,1-dioxide
N-diaminomethylene-2,3-dihydro-3-cyano-5-ethyl-1-benzothiophene-6-carboxamide-1,1-dioxide;

from methyl 2,3-dihydro-3-cyano-1-benzothiophene-6-carboxylate-1,1-dioxide
N-diaminomethylene-2,3-dihydro-3-cyano-1-benzothiophene-6-carboxamide-1,1-dioxide;

from methyl 2,3-dihydro-3-cyano-3-methyl-1-benzothiophene-6-carboxylate-1,1-dioxide
N-diaminomethylene-2,3-dihydro-3-cyano-3-methyl-1-benzothiophene-6-carboxamide-1,1-dioxide;

from methyl 2,3-dihydro-3-amino-5-methyl-1-benzothiophene-6-carboxylate-1,1-dioxide
N-diaminomethylene-2,3-dihydro-3-amino-5-methyl-1-benzothiophene-6-carboxamide-1,1-dioxide;

from methyl 2,3-dihydro-3-amino-3-methyl-5-ethyl-1-benzothiophene-6-carboxylate-1,1-dioxide
N-diaminomethylene-2,3-dihydro-3-amino-3-methyl-5-ethyl-1-benzothiophene-6-carboxamide-1,1-dioxide;

from methyl 2,3-dihydro-3-amino-5-ethyl-1-benzothiophene-6-carboxylate-1,1-dioxide
N-diaminomethylene-2,3-dihydro-3-amino-5-ethyl-1-benzothiophene-6-carboxamide-1,1-dioxide;

from methyl 2,3-dihydro-3-amino-1-benzothiophene-6-carboxylate-1,1-dioxide
N-diaminomethylene-2,3-dihydro-3-amino-1-benzothiophene-6-carboxamide-1,1-dioxide;

from methyl 2,3-dihydro-3-amino-3-methyl-1-benzothiophene-6-carboxylate-1,1-dioxide
N-diaminomethylene-2,3-dihydro-3-amino-3-methyl-1-benzothiophene-6-carboxamide-1,1-dioxide;

from methyl 2,3-dihydro-3-N-methylamino-5-methyl-1-benzothiophene-6-carboxylate-1,1-dioxide
N-diaminomethylene-2,3-dihydro-3-N-methylamino-5-methyl-1-benzothiophene-6-carboxamide-1,1-dioxide;

from methyl 2,3-dihydro-3-N-methylamino-3-methyl-5-ethyl-1-benzothiophene-6-carboxylate-1,1-dioxide
N-diaminomethylene-2,3-dihydro-3-N-methylamino-3-methyl-5-ethyl-1-benzothiophene-6-carboxamide-1,1-dioxide;

from methyl 2,3-dihydro-3-N-methylamino-5-ethyl-1-benzothiophene-6-carboxylate-1,1-dioxide
N-diaminomethylene-2,3-dihydro-3-N-methylamino-5-ethyl-1-benzothiophene-6-carboxamide-1,1-dioxide;

from methyl 2,3-dihydro-3-N-methylamino-1-benzothiophene-6-carboxylate-1,1-dioxide
N-diaminomethylene-2,3-dihydro-3-N-methylamino-1-benzothiophene-6-carboxamide-1,1-dioxide;

from methyl 2,3-dihydro-3-N-methylamino-3-methyl-1-benzothiophene-6-carboxylate-1,1-dioxide
N-diaminomethylene-2,3-dihydro-3-N-methylamino-3-methyl-1-benzothiophene-6-carboxamide-1,1-dioxide;

from methyl 2,3-dihydro-3-N,N-dimethylamino-5-methyl-1-benzothiophene-6-carboxylate-1,1-dioxide
N-diaminomethylene-2,3-dihydro-3-N,N-dimethylamino-5-methyl-1-benzothiophene-6-carboxamide-1,1-dioxide;

from methyl 2,3-dihydro-3-N,N-dimethylamino-3-methyl-5-ethyl-1-benzothiophene-6-carboxylate-1,1-dioxide
N-diaminomethylene-2,3-dihydro-3-N,N-dimethylamino-3-methyl-5-ethyl-1-benzothiophene-6-carboxamide-1,1-dioxide;

from methyl 2,3-dihydro-3-N,N-dimethylamino-5-ethyl-1-benzothiophene-6-carboxylate-1,1-dioxide
N-diaminomethylene-2,3-dihydro-3-N,N-dimethylamino-5-ethyl-1-benzothiophene-6-carboxamide-1,1-dioxide;

from methyl 2,3-dihydro-3-N,N-dimethylamino-1-benzothiophene-6-carboxylate-1,1-dioxide
N-diaminomethylene-2,3-dihydro-3-N,N-dimethylamino-1-benzothiophene-6-carboxamide-1,1-dioxide;

from methyl 2,3-dihydro-3-N,N-dimethylamino-3-methyl-1-benzothiophene-6-carboxylate-1,1-dioxide
N-diaminomethylene-2,3-dihydro-3-N,N-dimethylamino-3-methyl-1-benzothiophene-6-carboxamide-1,1-dioxide;

from methyl 2,3-dihydro-3-methyl-5-ethyl-1-benzothiophene-6-carboxylate-1,1-dioxide
N-diaminomethylene-2,3-dihydro-3-methyl-5-ethyl-1-benzothiophene-6-carboxamide-1,1-dioxide;

from methyl 2,3-dihydro-3-oxo-5-methyl-1-benzothiophene-6-carboxylate-1,1-dioxide
N-diaminomethylene-2,3-dihydro-3-oxo-5-methyl-1-benzothiophene-6-carboxamide-1,1-dioxide;

from methyl 2,3-dihydro-3-oxo-5-ethyl-1-benzothiophene-6-carboxylate-1-1-dioxide
N-diaminomethylene-2,3-dihydro-3-oxo-5-ethyl-1-benzothiophene-6-carboxamide-1,1-dioxide;

from methyl 2,3-dihydro-3-oxo-5-fluoro-1-benzothiophene-6-carboxylate-1,1-dioxide
N-diaminomethylene-2,3-dihydro-3-oxo-5-fluoro-1-benzothiophene-6-carboxamide-1,1-dioxide;

from methyl 2,3-dihydro-3-oxo-1-benzothiophene-6-carboxylate-1-1-dioxide
N-diaminomethylene-2,3-dihydro-3-oxo-1-benzothiophene-6-carboxamide-1,1-dioxide;

from methyl 2,3-dihydro-3-oxo-5-trifluoromethyl-1-benzothiophene-6-carboxylate-1,1-dioxide
N-diaminomethylene-2,3-dihydro-3-oxo-5-trifluoromethyl-1-benzothiophene-6-carboxamide-1,1-dioxide;

from methyl 2,3-dihydro-3,3-ethylenedioxy-5-methyl-1-benzothiophene-6-carboxylate-1,1-dioxide
N-diaminomethylene-2,3-dihydro-3,3-ethylenedioxy-5-methyl-1-benzothiophene-6-carboxamide-1,1-dioxide, m.p. 242°, methanesulfonate: 285–287°;
from methyl 2,3-dihydro-3,3-ethylenedioxy-5-ethyl-1-benzothiophene-6-carboxylate-1,1-dioxide
N-diaminomethylene-2,3-dihydro-3,3-ethylenedioxy-5-ethyl-1-benzothiophene-6- carboxamide-1,1-dioxide;
from methyl 2,3-dihydro-3,3-ethylenedioxy-5-fluoro-1-benzothiophene-6-carboxylate-1,1-dioxide
N-diaminomethylene-2,3-dihydro-3,3-ethylenedioxy-5-fluoro-1-benzothiophene-6-carboxamide-1,1-dioxide;
from methyl 2,3-dihydro-3,3-ethylenedioxy-1-benzothiophene-6-carboxylate-1,1-dioxide
N-diaminomethylene-2,3-dihydro-3,3-ethylenedioxy-1-benzothiophene-6-carboxamide-1,1-dioxide;
from methyl 2,3-dihydro-3,3-ethylenedioxy-5-trifluoromethyl-1-benzothiophene-6-carboxylate-1,1-dioxide
N-diaminomethylene-2,3-dihydro-3,3-ethylenedioxy-5-trifluoromethyl-1-benzothiophene-6-carboxamide-1,1-dioxide;
from methyl 2,3-dihydro-3-hydroxyimino-5-methyl-1-benzothiophene-6-carboxylate-1,1-dioxide
N-diaminomethylene-2,3-dihydro-3-hydroxyimino-5-methyl-1-benzothiophene-6-carboxamide-1,1-dioxide, m.p. 250° (methanesulfonate);
from methyl 2,3-dihydro-3-hydroxyimino-5-ethyl-1-benzothiophene-6-carboxylate-1,1-dioxide
N-diaminomethylene-2,3-dihydro-3-hydroxyimino-5-ethyl-1-benzothiophene-6-carboxamide-1,1-dioxide;
from methyl 2,3-dihydro-3-hydroxyimino-5-fluoro-1-benzothiophene-6-carboxylate-1,1-dioxide
N-diaminomethylene-2,3-dihydro-3-hydroxyimino-5-fluoro-1-benzothiophene-6-carboxamide-1,1-dioxide;
from methyl 2,3-dihydro-3-hydroxyimino-2,2,5-trimethyl-1-benzothiophene-6-carboxylate-1,1-dioxide
N-diaminomethylene-2,3-dihydro-3-hydroxyimino-2,2,5-trimethyl-1-benzothiophene-6-carboxamide-1,1-dioxide, m.p. 237–238°0 (methanesulfonate);
from methyl 2,3-dihydro-3-hydroxyimino-5-trifluoromethyl-1-benzothiophene-6-carboxylate-1,1-dioxide
N-diaminomthylene-2,3-dihydro-3-hydroxyimino-5-trifluoromethyl-1-benzothiophene-6-carboxamide-1,1-dioxide;
from methyl 2,3-dihydro-3-methoxyimino-5-methyl-1-benzothiophene-6-carboxylate-1,1-dioxide
N-diaminomethylene-2,3-dihydro-3-methoxyimino-5-methyl-1-benzothiophene-6-carboxamide-1,1-dioxide, m.p. 284° (methanesulfonate);
from methyl 2,3-dihydro-3-methoxyimino-5-ethyl-1-benzothiophene-6-carboxylate-1,1-dioxide
N-diaminomethylene-2,3-dihydro-3-methoxyimino-5-ethyl-1-benzothiophene-6-carboxamide-1,1-dioxide;
from methyl 2,3-dihydro-3-methoxyimino-5-fluoro-1-benzothiophene-6-carboxylate-1,1-dioxide
N-diaminomethylene-2,3-dihydro-3-methoxyimino-5-fluoro-1-benzothiophene-6-carboxamide-1,1-dioxide;
from methyl 2,3-dihydro-3-methoxyimino-1-benzothiophene-6-carboxylate-1,1-dioxide
N-diaminomethylene-2,3-dihydro-3-methoxyimino-1-benzothiophene-6-carboxamide-1,1-dioxide;
from methyl 2,3-dihydro-3-methoxyimino-5-trifluoromethyl-1-benzothiophene-6-carboxylate-1,1-dioxide
N-diaminomethylene-2,3-dihydro-3-methoxyimino-5-trifluoromethyl-1-benzothiophene-6-carboxamide-1,1-dioxide;
from methyl 2,3-dihydro-3-methoxy-1-benzothiophene-6-carboxylate-1,1-dioxide
N-diaminomethylene-2,3-dihydro-3-methoxy-1-benzothiophene-6-carboxamide-1,1-dioxide, m.p. 193–194°, methanesulfonate: m.p. 234–236°;
from methyl 2,3-dihydro-3-methoxy-5-methyl-1-benzothiophene-6-carboxylate-1,1-dioxide
N-diaminomethylene-2,3-dihydro-3-methoxy-5-methyl-1-benzothiophene-6-carboxamide-1,1-dioxide, m.p. 224°, methanesulfonte: m.p. 249–251°.

EXAMPLE 2

1.24 g of sodium are introduced into 20 ml of dry methanol with exclusion of moisture, under a nitrogen atmosphere and with stirring. The solution is then treated at room temperature with 5.64 g of guanidine hydrochloride and additionally stirred for 30 minutes. It is then filtered, the filtrate is concentrated in vacuo, and the residue is treated with 10 ml of ethylene glycol dimethyl ether (EDME) and again freed from the solvent. The residue is taken up in 8 ml of EDME and a suspension of 2.1 g of 2,3-dihydro-3,5-dimethyl-1-benzothiophene-6-carbonyl chloride-1,1-dioxide [obtainable by reaction of 1.9 g of 2,3-dihydro-3,5-dimethyl-1-benzothiophene-6-carboxylic acid 1,1-dioxide with 10 ml of thionyl chloride with exclusion of moisture and with stirring for 4 hours at boiling heat] in 10 ml of EDME is added dropwise with stirring at 5 to 100 in the course of 45 minutes. The reaction mixture is then allowed to cool to room temperature and is stirred for 1 hour, then it is treated with ice-cooling with 60 ml of water and the resulting precipitate is filtered off. After recrystallization from dichloromethane/methanol, N-diaminomethylene-2,3-dihydro-3,5-dimethyl-1-benzothiophene-6-carboxamide-1,1-dioxide, m.p. 237–238°, is obtained. By treatment with methanesulfonic acid in 30 ml of methanol at 40° C. for a period of 2 hours, the corresponding methanesulfonate is obtained: M.p. 245–248°.

The following are obtained analogously
from methyl 2,3-dihydro-5-methyl-1-benzothiophene-6-carboxylate-1,1-dioxide
N-diaminomethylene-2,3-dihydro-5-methyl-1-benzothiophene-6-carboxamide-1,1-dioxide, m.p. 299–301° (methanesulfonate);
from methyl 2,3-dihydro-5-ethyl-1-benzothiophene-6-carboxylate-1,1-dioxide
N-diaminomethylene-2,3-dihydro-5-ethyl-1-benzothiophene-6-carboxamide-1,1-dioxide;
from methyl 2,3-dihydro-5-trifluoromethyl-1-benzothiophene-6-carboxylate-1,1-dioxide
N-diaminomethylene-2,3-dihydro-5-trifluoromethyl-1-benzothiophene-6-carboxamide-1,1-dioxide;
from methyl 2,3-dihydro-1-benzothiophene-6-carboxylate-1,1-dioxide
N-diaminomethylene-2,3-dihydro-1-benzothiophene-6-carboxamide-1,1-dioxide, m.p. 223°, methanesulfonate: m.p. 264–265°;
from methyl 2,3-dihydro-3-methyl-5-fluoro-1-benzothiophene-6-carboxylate-1,1-dioxide
N-diaminomethylene-2,3-dihydro-3-methyl-5-fluoro-1-benzothiophene-6-carboxamide-1,1-dioxide;
from methyl 2,3-dihydro-3-isopropyl-5-methyl-1-benzothiophene-6-carboxylate-1,1-dioxide
N-diaminomethylene-2,3-dihydro-3-isopropyl-5-methyl-1-benzothiophene-6-carboxamide-1,1-dioxide, m.p. 194–196°;

from methyl 2,3-dihydro-3-methyl-1-benzothiophene-6-carboxylate-1,1-dioxide
N-diaminomethylene-2,3-dihydro-3-methyl-1-benzothiophene-6-carboxamide-1,1-dioxide;
from methyl 2,3-dihydro-3,3-dimethyl-5-fluoro-1-benzothiophene-6-carboxylate-1,1-dioxide
N-diaminomethylene-2,3-dihydro-3,3-dimethyl-5-fluoro-1-benzothiophene-6-carboxamide-1,1-dioxide;
from methyl 2,3-dihydro-3,3-dimethyl-5-ethyl-1-benzothiophene-6-carboxylate-1,1-dioxide
N-diaminomethylene-2,3-dihydro-3,3,5-trimethyl-1-benzothiophene-6-carboxamide-1,1-dioxide;
from methyl 2,3-dihydro-3,3,5-trimethyl-1-benzothiophene-6-carboxylate-1,1-dioxide
N-diaminomethylene-2,3-dihydro-3,3-dimethyl-5-fluoro-1-benzothiophene-6-carboxamide-1,1-dioxide;
from methyl 2,3-dihydro-3,3-dimethyl-5-trifluoromethyl-1-benzothiophene-6-carboxylate-1,1-dioxide
N-diaminomethylene-2,3-dihydro-3,3-dimethyl-5-trifluoromethyl-1-benzothiophene-6-carboxamide-1,1-dioxide;
from methyl 2,3-dihydro-3,3-dimethyl-1-benzothiophene-6-carboxylate-1,1-dioxide
N-diaminomethylene-2,3-dihydro-3,3-dimethyl-1-benzothiophene-6-carboxamide-1,1-dioxide;
from methyl 2,3-dihydro-2,2-dimethyl-5-fluoro-1-benzothiophene-6-carboxylate-1,1-dioxide
N-diaminomethylene-2,3-dihydro-2,2-dimethyl-5-fluoro-1-benzothiophene-6-carboxamide-1,1-dioxide;
from methyl 2,3-dihydro-2,2-dimethyl-5-ethyl-1-benzothiophene-6-carboxylate-1,1-dioxide
N-diaminomethylene-2,3-dihydro-2,2-dimethyl-5-ethyl-1-benzothiophene-6-carboxamide-1,1-dioxide;
from methyl 2,3-dihydro-2,2,5-trimethyl-1-benzothiophene-6-carboxylate-1,1-dioxide
N-diaminomethylene-2,3-dihydro-2,2-dimethyl-5-fluoro-1-benzothiophene-6-carboxamide-1,1-dioxide;
from methyl 2,3-dihydro-2,2,5-trimethyl-3-methoxy-1-benzothiophene-6-carboxylate-1,1-dioxide
N-diaminomethylene-2,3-dihydro-2,2,5-trimethyl-3-methoxy-1-benzothiophene-6-carboxamide-1,1-dioxide, m.p. 245°, methanesulfonate: 284–285°;
from methyl 2,3-dihydro-2,2-dimethyl-1-benzothiophene-6-carboxylate-1,1-dioxide
N-diaminomethylene-2,3-dihydro-2,2-dimethyl-1-benzothiophene-6-carboxamide-1,1-dioxide;
from methyl 2,3-dihydro-2,5-dimethyl-1-benzothiophene-6-carboxylate-1,1-dioxide
N-diaminomethylene-2,3-dihydro-2,5-dimethyl-1-benzothiophene-6-carboxamide-1,1-dioxide;
from methyl 2,3-dihydro-2-methyl-5-ethyl-1-benzothiophene-6-carboxylate-1,1-dioxide
N-diaminomethylene-2,3-dihydro-2-methyl-5-ethyl-1-benzothiophene-6-carboxamide-1,1-dioxide;
from methyl 2,3-dihydro-2-methyl-5-trifluoromethyl-1-benzothiophene-6-carboxylate-1,1-dioxide
N-diaminomethylene-2,3-dihydro-2-methyl-5-trifluoromethyl-1-benzothiophene-6-carboxamide-1,1-dioxide;
from methyl 2,3-dihydro-2-methyl-1-benzothiophene-6-carboxylate-1,1-dioxide
N-diaminomethylene-2,3-dihydro-2-methyl-1-benzothiophene-6-carboxamide-1,1-dioxide.

EXAMPLE 3

213 mg of sodium are introduced into 5 ml of methanol under a nitrogen gas atmosphere, with stirring and exclusion of moisture. The solution obtained is treated at room temperature with 975 mg of guanidine hydrochloride and stirred for 30 minutes. The suspension is then filtered. After this, the filtrate is treated with 500 mg of methyl 4-acetyl-2-methyl-5-methylsulfonylbenzoate and refluxed for 1 hour. After additional stirring at room temperature for 1 hour, the mixture is treated with water with ice-cooling, saturated with sodium chloride and extracted with ethyl acetate, and the organic phase is washed with water, dried and concentrated. Recrystallization from methanol/ethyl acetate gives N-diaminomethylene-2,3-dihydro-3-hydroxy-3,5-dimethyl-1-benzothiophene-6-carboxamide-1,1-dioxide, m.p. 243–245°. Treatment with methanesulfonic acid in methanol gives, after recrystallization from methanol/acetone, the corresponding methanesulfonate: m.p. 214–216°.

The following are obtained analogously
from methyl 4-benzoyl-5-methylsulfonyl benzoate
N-diaminomethylene-2,3-dihydro-3-phenyl-3-hydroxy-1-benzothiophene-6-carboxamide-1,1- dioxide;
from methyl 4-benzoyl-2-methyl-5-methylsulfonyl benzoate
N-diaminomethylene-2,3-dihydro-3-phenyl-3-hydroxy-5-methyl-1-benzothiophene-6-carboxamide-1,1-dioxide

EXAMPLE 4

A guanidine solution prepared—as described in Example 3—from 547 mg of sodium, 12 ml of methanol and 2.5 g of guanidine hydrochloride is treated with 1.2 g of methyl 2,3-dihydro-5-methyl-3-methylene-1-benzothiophene-6-carboxylate-1,1-dioxide [prepared by cyclization of methyl 4-acetyl-2-methyl-5-methylsulfonylbenzoate and subsequent dehydration] and the mixture is boiled for 1 hour, then stirred at room temperature for a further hour and worked up in the customary manner. N-Diaminomethylene-2,3-dihydro-3-methoxy-3,5-dimethyl-1-benzothiophene-6-carboxamide-1,1-dioxide is obtained. Treatment with methanesulfonic acid in methanol gives the corresponding methanesulfonate, m.p. 214–215°.
The following are obtained analogously
from methyl 3-phenyl-1-benzothiophene-6-carboxylate-1,1-dioxide
N-diaminomethylene-2,3-dihydro-3-phenyl-3-methoxy-1-benzothiophene-6-carboxamide-1,1-dioxide;
from methyl 5-methyl-3-phenyl-1-benzothiophene-6-carboxylate-1,1-dioxide
N-diaminomethylene-2,3-dihydro-3-phenyl-3-methoxy-5-methyl-1-benzothiophene-6-carboxamide-1,1-dioxide.

EXAMPLE 5

Analogously to Example 2, reaction of freshly prepared guanidine with 3,5-dimethyl-1-benzothiophene-6-carbonyl chloride-1,1-dioxide [obtainable by reaction of 1.9 g of 3,5-dimethyl-1-benzothiophene-6-carboxylic acid 1,1-dioxide with 10 ml of thionyl chloride with exclusion of moisture and with stirring for 4 hours at boiling heat] gives N-diaminomethylene-3,5-dimethyl-1-benzothiophene-6-carboxamide-1,1-dioxide. Treatment with methanesulfonic acid in methanol gives the corresponding methanesulfonate.
The following are obtained analogously
from methyl 5-methyl-1-benzothiophene-6-carboxylate-1,1-dioxide
N-diaminomethylene-5-methyl-1-benzothiophene-6-carboxamide-1,1-dioxide;

from methyl 5-ethyl-1-benzothiophene-6-carboxylate-1,1-dioxide
N-diaminomethylene-5-ethyl-1-benzothiophene-6-carboxamide-1,1-dioxide;
from methyl 5-trifluoromethyl-1-benzothiophene-6-carboxylate-1,1-dioxide
N-diaminomethylene-5-trifluoromethyl-1-benzothiophene-6-carboxamide-1,1-dioxide;
from methyl 1-benzothiophene-6-carboxylate-1,1-dioxide
N-diaminomethylene-1-benzothiophene-6-carboxamide-1,1-dioxide;
from methyl 3-methyl-5-ethyl-1-benzothiophene-6-carboxylate-1,1-dioxide
N-diaminomethylene-3-methyl-5-ethyl-1-benzothiophene-6-carboxamide-1,1-dioxide;
from methyl 3-methyl-5-fluoro-1-benzothiophene-6-carboxylate-1,1-dioxide
N-diaminomethylene-3-methyl-5-fluoro-1-benzothiophene-6-carboxamide-1,1-dioxide;
from methyl 3-methyl-5-trifluoromethyl-1-benzothiophene-6-carboxylate-1,1-dioxide
N-diaminomethylene-3-methyl-5-trifluoromethyl-1-benzothiophene-6-carboxamide-1,1-dioxide;
from methyl 3-phenyl-5-methyl-1-benzothiophene-6-carboxylate-1,1-dioxide
N-diaminomethylene-3-phenyl-5-methyl-1-benzothiophene-6-carboxamide-1,1-dioxide;
from methyl 3-phenyl-5-ethyl-1-benzothiophene-6-carboxylate-1,1-dioxide
N-diaminomethylene-3-phenyl-5-ethyl-1-benzothiophene-6-carboxamide-1,1-dioxide;
from methyl 3-phenyl-1-benzothiophene-6-carboxylate-1,1-dioxide
N-diaminomethylene-3-phenyl-1-benzothiophene-6-carboxamide-1,1-dioxide;
from methyl 3-methyl-1-benzothiophene-6-carboxylate-1,1-dioxide
N-diaminomethylene-3-methyl-1-benzothiophene-6-carboxamide-1,1-dioxide;
from methyl 2,5-dimethyl-1-benzothiophene-6-carboxylate-1,1-dioxide
N-diaminomethylene-2,5-dimethyl-1-benzothiophene-6-carboxamide-1,1-dioxide;
from methyl 2-methyl-5-ethyl-1-benzothiophene-6-carboxylate-1,1-dioxide
N-diaminomethylene-2-methyl-5-ethyl-1-benzothiophene-6-carboxamide-1,1-dioxide;
from methyl 2-methyl-5-trifluoromethyl-1-benzothiophene-6-carboxylate-1,1-dioxide
N-diaminomethylene-2-methyl-5-trifluoromethyl-1-benzothiophene-6-carboxamide-1,1-dioxide;
from methyl 2-methyl-5-fluoro-1-benzothiophene-6-carboxylate-1,1-dioxide
N-diaminomethylene-2-methyl-5-fluoro-1-benzothiophene-6-carboxamide-1,1-dioxide;
from methyl 2-methyl-1-benzothiophene-6-carboxylate-1,1-dioxide
N-diaminomethylene-2-methyl-1-benzothiophene-6-carboxamide-1,1-dioxide;
from methyl 2,3-dihydro-3-methylene-5-ethyl-1-benzothiophene-6-carboxylate-1,1-dioxide
N-diaminomethylene-2,3-dihydro-3-methylene-5-methyl-1-benzothiophene-6-carboxamide-1,1-dioxide, m.p. 208–212°, methanesulfonate: 230–235°;

from methyl 2,3-dihydro-3-methylene-5-ethyl-1-benzothiophene-6-carboxylate-1,1-dioxide
N-diaminomethylene-2,3-dihydro-3-methylene-5-ethyl-1-benzothiophene-6-carboxamide-1,1-dioxide;
from methyl 2,3-dihydro-3-oxo-2,2,5-trimethyl-1-benzothiophene-6-carboxylate-1,1-dioxide
N-diaminomethylene-2,3-dihydro-3-oxo-2,2,5-trimethyl-1-benzothiophene-6-carboxamide-1,1-dioxide, m.p. 250–251° (methanesulfonate);
from methyl 2,3-dihydro-3-methylene-5-fluoro-1-benzothiophene-6-carboxylate-1,1-dioxide
N-diaminomethylene-2,3-dihydro-3-methylene-5-fluoro-1-benzothiophene-6-carboxamide-1,1-dioxide;
from methyl 2,3-dihydro-3-methylene-5-trifluoromethyl-1-benzothiophene-6-carboxylate-1,1-dioxide
N-diaminomethylene-2,3-dihydro-3-methylene-5-trifluoromethyl-1-benzothiophene-6-carboxamide-1,1-dioxide;
from methyl 2,3-dihydro-3-methylene-1-benzothiophene-6-carboxylate-1,1-dioxide
N-diaminomethylene-2,3-dihydro-3-methylene-1-benzothiophene-6-carboxamide-1,1-dioxide.

EXAMPLE 6

Analogously to Example 1, the following are obtained
from methyl 6-methyl-1,3-benzoxathiole-5-carboxylate-3,3-dioxide
N-diaminomethylene-6-methyl-1,3-benzoxathiole-5-carboxamide-3,3-dioxide;
from methyl 1,3-benzoxathiole-5-carboxylate-3,3-dioxide
N-diaminomethylene-1,3-benzoxathiole-5-carboxamide-3,3-dioxide;
from methyl 6-ethyl-1,3-benzoxathiole-5-carboxylate-3,3-dioxide
N-diaminomethylene-6-ethyl-1,3-benzoxathiole-5-carboxamide-3,3-dioxide;
from methyl 2,6-dimethyl-1,3-benzoxathiole-5-carboxylate-3,3-dioxide
N-diaminomethylene-2,6-dimethyl-1,3-benzoxathiole-5-carboxamide-3,3-dioxide;
from methyl 2-methyl-1,3-benzoxathiole-5-carboxylate-3,3-dioxide
N-diaminomethylene-2-methyl-1,3-benzoxathiole-5-carboxamide-3,3-dioxide;
from methyl 2-methyl-6-ethyl-1,3-benzoxathiole-5-carboxylate-3,3-dioxide
N-diaminomethylene-2-methyl-6-ethyl-1,3-benzoxathiole-5-carboxamide-2-3,3-dioxide [sic];
from methyl 2,2,6-trimethyl-1,3-benzoxathiole-5-carboxylate-3,3-dioxide
N-diaminomethylene-2,2,6-trimethyl-1,3-benzoxathiole-5-carboxamide-3,3-dioxide;
from methyl 2,2-dimethyl-1,3-benzoxathiole-5-carboxylate-3,3-dioxide
N-diaminomethylene-2,2-dimethyl-1,3-benzoxathiole-5-carboxamide-3,3-dioxide;
from methyl 2,2-dimethyl-6-ethyl-1,3-benzoxathiole-5-carboxylate-3,3-dioxide
N-diaminomethylene-2,2-dimethyl-6-ethyl-1,3-benzoxathiole-5-carboxamide-3,3-dioxide;
from methyl 2,5-dimethyl-2,3-dihydrobenzothiazole-6-carboxylate-1,1-dioxide
6-N-diaminomethylenecarbamoyl-2,5-dimethyl-2,3-dihydrobenzothiazole-,1,1-dioxide;

from methyl 2-methyl-2,3-dihydrobenzothiazole-5-carboxylate-1,1-dioxide
  6-N-diaminomethylenecarbamoyl-2-methyl-2,3-dihydrobenzothiazole-1,1-dioxide;
from methyl 2-methyl-6-ethyl-2,3-dihydrobenzothiazole-5-carboxylate-1,1-dioxide
  6-N-diaminomethylenecarbamoyl-2-methyl-6-ethyl-2,3-dihydrobenzothiazole-1,1-dioxide;
from methyl 2,3,5-trimethyl-2,3-dihydrobenzothiazole-6-carboxylate-1,1-dioxide
  6-N-diaminomethylenecarbamoyl-2,3,5-trimethyl-2,3-dihydrobenzothiazole-1,1-dioxide;
from methyl 2,3-dimethyl-2,3-dihydrobenzothiazole-5-carboxylate-1,1-dioxide
  6-N-diaminomethylenecarbamoyl-2,3-dimethyl-2,3-dihydrobenzothiazole-1,1-dioxide;
from methyl 2,3-dimethyl-5-ethyl-2,3-dihydrobenzothiazole-5-carboxylate-1,1-dioxide
  6-N-diaminomethylenecarbamoyl-2,3-dimethyl-5-ethyl-2,3-dihydrobenzothiazole-1,1-dioxide;
from methyl 5-methyl-2,3-dihydrobenzothiazole-6-carboxylate-1,1-dioxide
  6-N-diaminomethylenecarbamoyl-5-methyl-2,3-dihydrobenzothiazole-1,1-dioxide;
from methyl 2,3-dihydrobenzothiazole-5-carboxylate-1,1-dioxide
  6-N-diaminomethylenecarbamoyl-2,3-dihydrobenzothiazole-1,1-dioxide;
from methyl 6-ethyl-2,3-dihydrobenzothiazole-5-carboxylate-1,1-dioxide
  6-N-diaminomethylenecarbamoyl-6-ethyl-2,3-dihydrobenzothiazole-1,1-dioxide;
from methyl 3,5-dimethyl-2,3-dihydrobenzothiazole-6-carboxylate-1,1-dioxide
  6-N-diaminomethylenecarbamoyl-3,5-dimethyl-2,3-dihydrobenzothiazole-1,1-dioxide;
from methyl 3-methyl-2,3-dihydrobenzothiazole-5-carboxylate-1,1-dioxide
  6-N-diaminomethylenecarbamoyl-3-methyl-2,3-dihydrobenzothiazole-1,1-dioxide;
from methyl 3-methyl-5-ethyl-2,3-dihydrobenzothiazole-5-carboxylate-1,1-dioxide
  6-N-diaminomethylenecarbamoyl-3-methyl-5-ethyl-2,3-dihydrobenzothiazole-1,1-dioxide;
from methyl 2,2,5-trimethyl-2,3-dihydrobenzothiazole-6-carboxylate-1,1-dioxide
  6-N-diaminomethylenecarbamoyl-2,2,5-trimethyl-2,3-dihydrobenzothiazole-1,1-dioxide;
from methyl 2,2-dimethyl-2,3-dihydrobenzothiazole-5-carboxylate-1,1-dioxide
  6-N-diaminomethylenecarbamoyl-2,2-dimethyl-2,3-dihydrobenzothiazole-1,1-dioxide;
from methyl 2,2-dimethyl-6-ethyl-2,3-dihydrobenzothiazole-5-carboxylate-1,1-dioxide
  6-N-diaminomethylenecarbamoyl-2,2-dimethyl-6-ethyl-2,3-dihydrobenzothiazole-1,1-dioxide;
from methyl 2,2,3,5-tetramethyl-2,3-dihydrobenzothiazole-6-carboxylate-1,1-dioxide
  6-N-diaminomethylenecarbamoyl-2,2,3,5-tetramethyl-2,3-dihydrobenzothiazole-1,1-dioxide;
from methyl 2,2,3-trimethyl-2,3-dihydrobenzothiazole-5-carboxylate-1,1-dioxide
  6-N-diaminomethylenecarbamoyl-2,2,3-trimethyl-2,3-dihydrobenzothiazole-1,1-dioxide;
from methyl 2,2,3-trimethyl-5-ethyl-2,3-dihydrobenzothiazole-5-carboxylate-1,1-dioxide
  6-N-diaminomethylenecarbamoyl-2,2,3-trimethyl-5-ethyl-2,3-dihydrobenzothiazole-1,1-dioxide.

EXAMPLE 7

Analogously to Example 1, the following are obtained
from methyl 6-methylthiochroman-7-carboxylate-1,1-dioxide
  N-diaminomethylene-6-methylthiochroman-7-carboxamide-1,1-dioxide;
from methyl thiochroman-7-carboxylate-1,1-dioxide
  N-diaminomethylenethiochroman-7-carboxamide-1,1-dioxide;
from methyl 6-ethylthiochroman-7-carboxylate-1,1-dioxide
  N-diaminomethylene-6-ethylthiochroman-7-carboxamide-1,1-dioxide;
from methyl 2,6-dimethylthiochroman-7-carboxylate-1,1-dioxide
  N-diaminomethylene-2,6-dimethylthiochroman-7-carboxamide-1,1-dioxide;
from methyl 2-methylthiochroman-7-carboxylate-1,1-dioxide
  N-diaminomethylene-2-methylthiochroman-7-carboxamide-1,1-dioxide;
from methyl 2-methyl-6-ethylthiochroman-7-carboxylate-1,1-dioxide
  N-diaminomethylene-2-methyl-6-ethylthiochroman-7-carboxamide-1,1-dioxide;
from methyl 2,2,6-trimethylthiochroman-7-carboxylate-1,1-dioxide
  N-diaminomethylene-2,2,6-trimethylthiochroman-7-carboxamide-1,1-dioxide;
from methyl 2,2-dimethylthiochroman-7-carboxylate-1,1-dioxide
  N-diaminomethylene-2,2-dimethylthiochroman-7-carboxamide-1,1-dioxide;
from methyl 2,2-dimethyl-6-ethylthiochroman-7-carboxylate-1,1-dioxide
  N-diaminomethylene-2,2-dimethyl-6-ethylthiochroman-7-carboxamide-1,1-dioxide;
from methyl 3,6-dimethylthiochroman-7-carboxylate-1,1-dioxide
  N-diaminomethylene-3,6-dimethylthiochroman-7-carboxamide-1,1-dioxide;
from methyl 3-methylthiochroman-7-carboxylate-1,1-dioxide
  N-diaminomethylene-3-methylthiochroman-7-carboxamide-1,1-dioxide;
from methyl 3-methyl-6-ethylthiochroman-7-carboxylate-1,1-dioxide
  N-diaminomethylene-3-methyl-6-ethylthiochroman-7-carboxamide-1,1-dioxide;
from methyl 4,6-dimethylthiochroman-7-carboxylate-1,1-dioxide
  N-diaminomethylene-4,6-dimethylthiochroman-7-carboxamide-1,1-dioxide, m.p. 204–205°, methanesulfonate: 248–250°;
from methyl 4-methylthiochroman-7-carboxylate-1,1-dioxide
  N-diaminomethylene-4-methylthiochroman-7-carboxamide-1,1-dioxide;
from methyl 4-methyl-6-ethylthiochroman-7-carboxylate-1,1-dioxide N-diaminomethylene-4-methyl-6-ethylthiochroman-7-carboxamide-1,1-dioxide;
from methyl 3,3,6-trimethylthiochroman-7-carboxylate-1,1-dioxide
N-diaminomethylene-3,3,6-trimethylthiochroman-7-carboxamide-1,1-dioxide;
from methyl 3,3-dimethylthiochroman-7-carboxylate-1,1-dioxide
N-diaminomethylene-3,3-dimethylthiochroman-7-carboxamide-1,1-dioxide;
from methyl 3,3-dimethyl-6-ethylthiochroman-7-carboxylate-1,1-dioxide
N-diaminomethylene-3,3-dimethyl-6-ethylthiochroman-7-carboxamide-1,1-dioxide;
from methyl 4,4,6-trimethylthiochroman-7-carboxylate-1,1-dioxide
N-diaminomethylene-4,4,6-trimethylthiochroman-7-carboxamide-1,1-dioxide;
from methyl 4,4-dimethylthiochroman-7-carboxylate-1,1-dioxide
N-diaminomethylenethiochroman-4,4-dimethyl-7-carboxamide-1,1-dioxide;
from methyl 2,2,4,6-tetramethyl-thiochroman-7-carboxylate-1,1-dioxide
N-diaminomethylene-2,2,4,6-tetramethyl-thiochroman-7-carboxamide-1,1-dioxide, m.p. 256° (methanesulfonate);
from methyl 4,4-dimethyl-6-ethylthiochroman-7-carboxylate-1,1-dioxide
N-diaminomethylene-4,4-dimethyl-6-ethylthiochroman-7-carboxamide-1,1-dioxide;
from methyl 6-methyl-2H-1-benzothiopyran-7-carboxylate-1,1-dioxide
N-diaminomethylene-6-methyl-2H-1-benzothiopyran-7-carboxamide-1,1-dioxide;
from methyl 2H-1-benzothiopyran-7-carboxylate-1,1-dioxide
N-diaminomethylene-2H-1-benzothiopyran-7-carboxamide-1,1-dioxide;
from methyl 6-ethyl-2H-1-benzothiopyran-7-carboxylate-1,1-dioxide
N-diaminomethylene-6-ethyl-2H-1-benzothiopyran-7-carboxamide-1,1-dioxide;
from methyl 2,6-dimethyl-2H-1-benzothiopyran-7-carboxylate-1,1-dioxide
N-diaminomethylene-2,6-dimethyl-2H-1-benzothiopyran-7-carboxamide-1,1-dioxide;
from methyl 2-methyl-2H-1-benzothiopyran-7-carboxylate-1,1-dioxide
N-diaminomethylene-2-methyl-2H-1-benzothiopyran-7-carboxamide-1,1-dioxide;
from methyl 2-methyl-6-ethyl-2H-1-benzothiopyran-7-carboxylate-1,1-dioxide
N-diaminomethylene-2-methyl-6-ethyl-2H-1-benzothiopyran-7-carboxamide-1,1-dioxide;
from methyl 2,2,6-trimethyl-2H-1-benzothiopyran-7-carboxylate-1,1-dioxide
N-diaminomethylene-2,2,6-trimethyl-2H-1-benzothiopyran-7-carboxamide-1,1-dioxide;
from methyl 2,2-dimethyl-2H-1-benzothiopyran-7-carboxylate-1,1-dioxide
N-diaminomethylene-2,2-dimethyl-2H-1-benzothiopyran-7-carboxamide-1,1-dioxide;
from methyl 2,2-dimethyl-6-ethyl-2H-1-benzothiopyran-7-carboxylate-1,1-dioxide
N-diaminomethylene-2,2-dimethyl-6-ethyl-2H-1-benzothiopyran-7-carboxamide-1,1-dioxide;
from methyl 3,6-dimethyl-2H-1-benzothiopyran-7-carboxylate-1,1-dioxide
N-diaminomethylene-3,6-dimethyl-2H-1-benzothiopyran-7-carboxamide-1,1-dioxide;
from methyl 3-methyl-2H-1-benzothiopyran-7-carboxylate-1,1-dioxide
N-diaminomethylene-3-methyl-2H-1-benzothiopyran-7-carboxamide-1,1-dioxide;
from methyl 3-methyl-6-ethyl-2H-1-benzothiopyran-7-carboxylate-1,1-dioxide
N-diaminomethylene-3-methyl-6-ethyl-2H-1-benzothiopyran-7-carboxamide-1,1-dioxide;
from methyl 4,6-dimethyl-2H-1-benzothiopyran-7-carboxylate-1,1-dioxide
N-diaminomethylene-4,6-dimethyl-2H-1-benzothiopyran-7-carboxamide-1,1-dioxide;
from methyl 4-methyl-2H-1-benzothiopyran-7-carboxylate-1,1-dioxide
N-diaminomethylene-4-methyl-2H-1-benzothiopyran-7-carboxamide-1,1-dioxide;
from methyl 4-methyl-6-ethyl-2H-1-benzothiopyran-7-carboxylate-1,1-dioxide
N-diaminomethylene-4-methyl-6-ethyl-2H-1-benzothiopyran-7-carboxamide-1,1-dioxide;
from methyl 6-methyl-4H-1-benzothiopyran-7-carboxylate-1,1-dioxide
N-diaminomethylene-6-methyl-4H-1-benzothiopyran-7-carboxamide-1,1-dioxide;
from methyl 4H-1-benzothiopyran-7-carboxylate-1,1-dioxide
N-diaminomethylene-4H-1-benzothiopyran-7-carboxamide-1,1-dioxide;
from methyl 6-ethyl-4H-1-benzothiopyran-7-carboxylate-1,1-dioxide
N-diaminomethylene-6-ethyl-4H-1-benzothiopyran-7-carboxamide-1,1-dioxide;
from methyl 2,6-dimethyl-4H-1-benzothiopyran-7-carboxylate-1,1-dioxide
N-diaminomethylene-2,6-dimethyl-4H-1-benzothiopyran-7-carboxamide-1,1-dioxide;
from methyl 2-methyl-4H-1-benzothiopyran-7-carboxylate-1,1-dioxide
N-diaminomethylene-2-methyl-4H-1-benzothiopyran-7-carboxamide-1,1-dioxide;
from methyl 2-methyl-6-ethyl-4H-1-benzothiopyran-7-carboxylate-1,1-dioxide
N-diaminomethylene-2-methyl-6-ethyl-4H-1-benzothiopyran-7-carboxamide-1,1-dioxide;
from methyl 3,6-dimethyl-4H-1-benzothiopyran-7-carboxylate-1,1-dioxide
N-diaminomethylene-3,6-dimethyl-4H-1-benzothiopyran-7-carboxamide-1,1-dioxide;
from methyl 3-methyl-4H-1-benzothiopyran-7-carboxylate-1,1-dioxide
N-diaminomethylene-3-methyl-4H-1-benzothiopyran-7-carboxamide-1,1-dioxide;
from methyl 3-methyl-6-ethyl-4H-1-benzothiopyran-7-carboxylate-1,1-dioxide
N-diaminomethylene-3-methyl-6-ethyl-4H-1-benzothiopyran-7-carboxamide-1,1-dioxide;
from methyl 4,6-dimethyl-4H-1-benzothiopyran-7-carboxylate-1,1-dioxide N-diaminomethylene-4,6-dimethyl-4H-1-benzothiopyran-7-carboxamide-1,1-dioxide;

from methyl 4-methyl-4H-1-benzothiopyran-7-carboxylate-1,1-dioxide

N-diaminomethylene-4-methyl-4H-1-benzothiopyran-7-carboxamide-1,1-dioxide;

from methyl 4-methyl-6-ethyl-4H-1-benzothiopyran-7-carboxylate-1,1-dioxide

N-diaminomethylene-4-methyl-6-ethyl-4H-1-benzothiopyran-7-carboxamide-1,1-dioxide;

from methyl 3-hydroxy-6-methylthiochroman-7-carboxylate-1,1-dioxide

N-diaminomethylene-3-hydroxy-6-methylthiochroman-7-carboxamide-1,1-dioxide;

from methyl 3-hydroxythiochroman-7-carboxylate-1,1-dioxide

N-diaminomethylene-3-hydroxythiochroman-7-carboxamide-1,1-dioxide;

from methyl 3-hydroxy-6-ethylthiochroman-7-carboxylate-1,1-dioxide

N-diaminomethylene-3-hydroxy-6-ethylthiochroman-7-carboxamide-1,1-dioxide;

from methyl 4-hydroxy-6-methylthiochroman-7-carboxylate-1,1-dioxide

N-diaminomethylene-4-hydroxy-6-methylthiochroman-7-carboxamide-1,1-dioxide;

from methyl 4-hydroxythiochroman-7-carboxylate-1,1-dioxide

N-diaminomethylene-4-hydroxythiochroman-7-carboxamide-1,1-dioxide;

from methyl 4-hydroxy-6-ethylthiochroman-7-carboxylate-1,1-dioxide

N-diaminomethylene-4-hydroxy-6-ethylthiochroman-7-carboxamide-1,1-dioxide;

from methyl 3-oxo-6-methylthiochroman-7-carboxylate-1,1-dioxide

N-diaminomethylene-3-oxo-6-methylthiochroman-7-carboxamide-1,1-dioxide;

from methyl 3-oxothiochroman-7-carboxylate-1,1-dioxide

N-diaminomethylene-3-oxothiochroman-7-carboxamide-1,1-dioxide;

from methyl 3-oxo-6-ethylthiochroman-7-carboxylate-1,1-dioxide

N-diaminomethylene-3-oxo-6-ethylthiochroman-7-carboxamide-1,1-dioxide;

from methyl 4-oxo-6-methylthiochroman-7-carboxylate-1,1-dioxide

N-diaminomethylene-4-oxo-6-methylthiochroman-7-carboxamide-1,1-dioxide;

from methyl 4-oxothiochroman-7-carboxylate-1,1-dioxide

N-diaminomethylene-4-oxothiochroman-7-carboxamide-1,1-dioxide;

from methyl 4-oxo-6-ethylthiochroman-7-carboxylate-1,1-dioxide

N-diaminomethylene-4-oxo-6-ethylthiochroman-7-carboxamide-1,1-dioxide.

EXAMPLE 8

Analogously to Example 1, the following are obtained from methyl 7-methyl-1,4-benzoxathian-6-carboxylate-4,4-dioxide N-diaminomethylene-7-methyl-1,4-benzoxathian-6-carboxamide-4,4-dioxide;

from methyl 7-ethyl-1,4-benzoxathian-6-carboxylate-4,4-dioxide

N-diaminomethylene-7-ethyl-1,4-benzoxathian-6-carboxamide-4,4-dioxide;

from methyl 1,4-benzoxathian-6-carboxylate-4,4-dioxide

N-diaminomethylene-1,4-benzoxathian-6-carboxamide-4,4-dioxide;

from methyl 2,7-dimethyl-1,4-benzoxathian-6-carboxylate-4,4-dioxide

N-diaminomethylene-2,7-dimethyl-1,4-benzoxathian-6-carboxamide-4,4-dioxide;

from methyl 2-methyl-7-ethyl-1,4-benzoxathian-6-carboxylate-4,4-dioxide

N-diaminomethylene-2-methyl-7-ethyl-1,4-benzoxathian-6-carboxamide-4,4-dioxide;

from methyl 2-methyl-1,4-benzoxathian-6-carboxylate-4,4-dioxide

N-diaminomethylene-1,4-benzoxathian-2-methyl-6-carboxamide-4,4-dioxide;

from methyl 3,7-dimethyl-1,4-benzoxathian-6-carboxylate-4,4-dioxide

N-diaminomethylene-3,7-dimethyl-1,4-benzoxathian-6-carboxamide-4,4-dioxide;

from methyl 3-methyl-7-ethyl-1,4-benzoxathian-6-carboxylate-4,4-dioxide

N-diaminomethylene-3-methyl-7-ethyl-1,4-benzoxathian-6-carboxamide-4,4-dioxide;

from methyl 3-methyl-1,4-benzoxathian-6-carboxylate-4,4-dioxide

N-diaminomethylene-3-methyl-1,4-benzoxathian-6-carboxamide-4,4-dioxide;

from methyl 2,2,7-trimethyl-1,4-benzoxathian-6-carboxylate-4,4-dioxide

N-diaminomethylene-2,2,7-trimethyl-1,4-benzoxathian-6-carboxamide-4,4-dioxide;

from methyl 2,2-dimethyl-7-ethyl-1,4-benzoxathian-6-carboxylate-4,4-dioxide

N-diaminomethylene-2,2-dimethyl-7-ethyl-1,4-benzoxathian-6-carboxamide-4,4-dioxide;

from methyl 2,2-dimethyl-1,4-benzoxathian-6-carboxylate-4,4-dioxide

N-diaminomethylene-2,2-dimethyl-1,4-benzoxathian-6-carboxamide-4,4-dioxide;

from methyl 3,3,7-trimethyl-1,4-benzoxathian-6-carboxylate-4,4-dioxide

N-diaminomethylene-3,3,7-trimethyl-1,4-benzoxathian-6-carboxamide-4,4-dioxide, m.p. 243–244° (methanesulfonate);

from methyl 3,3-dimethyl-7-ethyl-1,4-benzoxathian-6-carboxylate-4,4-dioxide

N-diaminomethylene-3,3-dimethyl-7-ethyl-1,4-benzoxathian-6-carboxamide-4,4-dioxide;

from methyl 3,3-dimethyl-1,4-benzoxathian-6-carboxylate-4,4-dioxide

N-diaminomethylene-3,3-dimethyl-1,4-benzoxathian-6-carboxamide-4,4-dioxide;

from methyl 2-oxo-7-methyl-1,4-benzoxathian-6-carboxylate-4,4-dioxide

N-diaminomethylene-2-oxo-7-methyl-1,4-benzoxathian-6-carboxamide-4,4-dioxide;

from methyl 2-oxo-7-ethyl-1,4-benzoxathian-6-carboxylate-4,4-dioxide

N-diaminomethylene-2-oxo-7-ethyl-1,4-benzoxathian-6-carboxamide-4,4-dioxide;

from methyl 2-oxo-1,4-benzoxathian-6-carboxylate-4,4-dioxide

N-diaminomethylene-2-oxo-1,4-benzoxathian-6-carboxamide-4,4-dioxide.

EXAMPLE 9

Analogously to Example 1, the following are obtained
from methyl 6-methyl-3,1-benzoxathian-7-carboxylate-1,1-dioxide
N-diaminomethylene-6-methyl-3,1-benzoxathian-7-carboxamide-1,1-dioxide;
from methyl 6-ethyl-3,1-benzoxathian-7-carboxylate-1,1-dioxide
N-diaminomethylene-6-ethyl-3,1-benzoxathian-7-carboxamide-1,1-dioxide;
from methyl 3,1-benzoxathian-7-carboxylate-1,1-dioxide
N-diaminomethylene-3,1-benzoxathian-7-carboxamide-1,1-dioxide;
from methyl 2,6-dimethyl-3,1-benzoxathian-7-carboxylate-1,1-dioxide
N-diaminomethylene-2,6-dimethyl-3,1-benzoxathian-7-carboxamide-1,1-dioxide;
from methyl 2-methyl-6-ethyl-3,1-benzoxathian-7-carboxylate-1,1-dioxide
N-diaminomethylene-2-methyl-6-ethyl-3,1-benzoxathian-7-carboxamide-1,1-dioxide;
from methyl 2-methyl-3,1-benzoxathian-7-carboxylate-1,1-dioxide
N-diaminomethylene-3,1-benzoxathian-2-methyl-7-carboxamide-1,1-dioxide;
from methyl 4,6-dimethyl-3,1-benzoxathian-7-carboxylate-1,1-dioxide
N-diaminomethylene-4,6-dimethyl-3,1-benzoxathian-7-carboxamide-1,1-dioxide;
from methyl 4-methyl-6-ethyl-3,1-benzoxathian-7-carboxylate-1,1-dioxide
N-diaminomethylene-4-methyl-6-ethyl-3,1-benzoxathian-7-carboxamide-1,1-dioxide;
from methyl 4-methyl-3,1-benzoxathian-7-carboxylate-1,1-dioxide
N-diaminomethylene-3,1-benzoxathian-4-methyl-7-carboxamide-1,1-dioxide;
from methyl 2,6-trimethyl-3,1-benzoxathian-7-carboxylate-1,1-dioxide
N-diaminomethylene-2,2,6-trimethyl-3,1-benzoxathian-7-carboxamide-1,1-dioxide;
from methyl 2,2-dimethyl-6-ethyl-3,1-benzoxathian-7-carboxylate-1,1-dioxide
N-diaminomethylene-2,2-dimethyl-6-ethyl-3,1-benzoxathian-6-carboxamide-1,1-dioxide;
from methyl 2,2-dimethyl-3,1-benzoxathian-7-carboxylate-1,1-dioxide
N-diaminomethylene-2,2-dimethyl-3,1-benzoxathian-7-carboxamide-1,1-dioxide;
from methyl 4,4,6-trimethyl-3,1-benzoxathian-7-carboxylate-1,1-dioxide
N-diaminomethylene-4,4,6-trimethyl-3,1-benzoxathian-7-carboxamide-1,1-dioxide;
from methyl 4,4-dimethyl-6-ethyl-3,1-benzoxathian-7-carboxylate-1,1-dioxide
N-diaminomethylene-4,4-dimethyl-6-ethyl-3,1-benzoxathian-6-carboxamide-1,1-dioxide;
from methyl 4,4-dimethyl-3,1-benzoxathian-6-carboxylate-1,1-dioxide
N-diaminomethylene-4,4-dimethyl-3,1-benzoxathian-6-carboxamide-1,1-dioxide;
from methyl 4-oxo-6-methyl-3,1-benzoxathian-7-carboxylate-1,1-dioxide
N-diaminomethylene-4-oxo-6-methyl-3,1-benzoxathian-7-carboxamide-1,1-dioxide;
from methyl 4-oxo-6-ethyl-3,1-benzoxathian-7-carboxylate-1,1-dioxide
N-diaminomethylene-4-oxo-6-ethyl-3,1-benzoxathian-7-carboxamide-1,1-dioxide;
from methyl 4-oxo-3,1-benzoxathian-6-carboxylate-1,1-dioxide
N-diaminomethylene-4-oxo-3,1-benzoxathian-6-carboxamide-1,1-dioxide.

EXAMPLE 10

Analogously to Example 1, the following are obtained
from methyl 6-methyl-1,4-benzodithian-7-carboxylate-1,1-dioxide
N-diaminomethylene-6-methyl-1,4-benzodithian-7-carboxamide-1,1-dioxide;
from methyl 6-ethyl-1,4-benzodithian-7-carboxylate-1,1-dioxide
N-diaminomethylene-6-ethyl-1,4-benzodithian-7-carboxamide-1,1-dioxide;
from methyl 1,4-benzodithian-7-carboxylate-1,1-dioxide
N-diaminomethylene-1,4-benzodithian-7-carboxamide-1,1-dioxide;
from methyl 2,6-dimethyl-1,4-benzodithian-7-carboxylate-1,1-dioxide
N-diaminomethylene-2,6-dimethyl-1,4-benzodithian-7-carboxamide-1,1-dioxide;
from methyl 2-methyl-6-ethyl-1,4-benzodithian-7-carboxylate-1,1-dioxide
N-diaminomethylene-2-methyl-6-ethyl-1,4-benzodithian-7-carboxamide-1,1-dioxide;
from methyl 2-methyl-1,4-benzodithian-7-carboxylate-1,1-dioxide
N-diaminomethylene-2-methyl-1,4-benzodithian-7-carboxamide-1,1-dioxide;
from methyl 3,6-dimethyl-1,4-benzodithian-7-carboxylate-1,1-dioxide
N-diaminomethylene-3,6-dimethyl-1,4-benzodithian-7-carboxamide-1,1-dioxide;
from methyl 3-methyl-6-ethyl-1,4-benzodithian-7-carboxylate-1,1-dioxide
N-diaminomethylene-3-methyl-6-ethyl-1,4-benzodithian-7-carboxamide-1,1-dioxide;
from methyl 3-methyl-1,4-benzodithian-7-carboxylate-1,1-dioxide
N-diaminomethylene-3-methyl-1,4-benzodithian-7-carboxamide-1,1-dioxide;
from methyl 2,2,6-trimethyl-1,4-benzodithian-7-carboxylate-1,1-dioxide
N-diaminomethylene-2,2,6-trimethyl-1,4-benzodithian-7-carboxamide-1,1-dioxide;
from methyl 2,2-dimethyl-6-ethyl-1,4-benzodithian-7-carboxylate-1,1-dioxide
N-diaminomethylene-2,2-dimethyl-6-ethyl-1,4-benzodithian-6-carboxamide-1,1-dioxide;
from methyl 2,2-dimethyl-1,4-benzodithian-7-carboxylate-1,1-dioxide
N-diaminomethylene-2,2-dimethyl-1,4-benzodithian-7-carboxamide-1,1-dioxide;
from methyl 3,3,6-trimethyl-1,4-benzodithian-7-carboxylate-1,1-dioxide N-diaminomethylene-3,3,6-trimethyl-1,4-benzodithian-7-carboxamide-1,1-dioxide;
from methyl 3,3-dimethyl-6-ethyl-1,4-benzodithian-7-carboxylate-1,1-dioxide
    N-diaminomethylene-3,3-dimethyl-6-ethyl-1,4-benzodithian-6-carboxamide-1,1-dioxide;
from methyl 3,3-dimethyl-1,4-benzodithian-7-carboxylate-1,1-dioxide
    N-diaminomethylene-3,3-dimethyl-1,4-benzodithian-7-carboxamide-1,1-dioxide;
from methyl 2-oxo-6-methyl-1,4-benzodithian-7-carboxylate-1,1-dioxide
    N-diaminomethylene-2-oxo-6-methyl-1,4-benzodithian-7-carboxamide-1,1-dioxide;
from methyl 2-oxo-6-ethyl-1,4-benzodithian-7-carboxylate-1,1-dioxide
    N-diaminomethylene-2-oxo-6-ethyl-1,4-benzodithian-7-carboxamide-1,1-dioxide;
from methyl 2-oxo-1,4-benzodithian-7-carboxylate-1,1-dioxide
    N-diaminomethylene-2-oxo-1,4-benzodithian-7-carboxamide-1,1-dioxide;
from methyl 3-oxo-6-methyl-1,4-benzodithian-7-carboxylate-1,1-dioxide
    N-diaminomethylene-3-oxo-6-methyl-1,4-benzodithian-7-carboxamide-1,1-dioxide;
from methyl 3-oxo-6-ethyl-1,4-benzodithian-7-carboxylate-1,1-dioxide
    N-diaminomethylene-3-oxo-6-ethyl-1,4-benzodithian-7-carboxamide-1,1-dioxide;
from methyl 3-oxo-1,4-benzodithian-7-carboxylate-1,1-dioxide
    N-diaminomethylene-3-oxo-1,4-benzodithian-7-carboxamide-1,1-dioxide.

EXAMPLE 11

Analogously to Example 1, the following are obtained
from methyl 6-methyl-3,4-dihydro-2H-1,4-benzothiazine-7-carboxylate-1,1-dioxide
    7-N-diaminomethylenecarbamoyl-6-methyl-3,4-dihydro-2H-1,4-benzothiazine-1,1-dioxide;
from methyl 6-ethyl-3,4-dihydro-2H-1,4-benzothiazine-7-carboxylate-1,1-dioxide
    7-N-diaminomethylenecarbamoyl-6-ethyl-3,4-dihydro-2H-1,4-benzothiazine-1,1-dioxide;
from methyl 3,4-dihydro-2H-1,4-benzothiazine-7-carboxylate-1,1-dioxide
    7-N-diaminomethylenecarbamoyl-3,4-dihydro-2H-1,4-benzothiazine-1,1-dioxide;
from methyl 4,6-dimethyl-3,4-dihydro-2H-1,4-benzothiazine-7-carboxylate-1,1-dioxide
    7-N-diaminomethylenecarbamoyl-4,6-dimethyl-3,4-dihydro-2H-1,4-benzothiazine-1,1-dioxide;
from methyl 4-methyl-6-ethyl-3,4-dihydro-2H-1,4-benzothiazine-7-carboxylate-1,1-dioxide
    7-N-diaminomethylenecarbamoyl-4-methyl-6-ethyl-3,4-dihydro-2H-1,4-benzothiazine-1,1-dioxide;
from methyl 4-methyl-3,4-dihydro-2H-1,4-benzothiazine-7-carboxylate-1,1-dioxide
    7-N-diaminomethylenecarbamoyl-4-methyl-3,4-dihydro-2H-1,4-benzothiazine-1,1-dioxide;
from methyl 3,6-dimethyl-3,4-dihydro-2H-1,4-benzothiazine-7-carboxylate-1,1-dioxide
    7-N-diaminomethylenecarbamoyl-3,6-dimethyl-3,4-dihydro-2H-1,4-benzothiazine-1,1-dioxide;
from methyl 3-methyl-6-ethyl-3,4-dihydro-2H-1,4-benzothiazine-7-carboxylate-1,1-dioxide
    7-N-diaminomethylenecarbamoyl-3-methyl-6-ethyl-3,4-dihydro-2H-1,4-benzothiazine-1,1-dioxide;
from methyl 3-methyl-3,4-dihydro-2H-1,4-benzothiazine-7-carboxylate-1,1-dioxide
    7-N-diaminomethylenecarbamoyl-3-methyl-3,4-dihydro-2H-1,4-benzothiazine-1,1-dioxide;
from methyl 3,4,6-trimethyl-3,4-dihydro-2H-1,4-benzothiazine-7-carboxylate-1,1-dioxide
    7-N-diaminomethylenecarbamoyl-3,4,6-trimethyl-3,4-dihydro-2H-1,4-benzothiazine-1,1-dioxide;
from methyl 3,4-dimethyl-6-ethyl-3,4-dihydro-2H-1,4-benzothiazine-7-carboxylate-1,1-dioxide
    7-N-diaminomethylenecarbamoyl-3,4-dimethyl-6-ethyl-3,4-dihydro-2H-1,4-benzothiazine-1,1-dioxide;
from methyl 3,4-dimethyl-3,4-dihydro-2H-1,4-benzothiazine-7-carboxylate-1,1-dioxide
    7-N-diaminomethylenecarbamoyl-3,4-dimethyl-3,4-dihydro-2H-1,4-benzothiazine-1,1-dioxide;
from methyl 3,3,6-trimethyl-3,4-dihydro-2H-1,4-benzothiazine-7-carboxylate-1,1-dioxide
    7-N-diaminomethylenecarbamoyl-3,3,6-trimethyl-3,4-dihydro-2H-1,4-benzothiazine-1,1-dioxide;
from methyl 3,3-dimethyl-6-ethyl-3,4-dihydro-2H-1,4-benzothiazine-7-carboxylate-1,1-dioxide
    7-N-diaminomethylenecarbamoyl-3,3-dimethyl-6-ethyl-3,4-dihydro-2H-1,4-benzothiazine-1,1-dioxide;
from methyl 3,3-dimethyl-3,4-dihydro-2H-1,4-benzothiazine-7-carboxylate-1,1-dioxide
    7-N-diaminomethylenecarbamoyl-3,3-dimethyl-3,4-dihydro-2H-1,4-benzothiazine-1,1-dioxide;
from methyl 3,3,4,6-tetramethyl-3,4-dihydro-2H-1,4-benzothiazine-7-carboxylate-1,1-dioxide
    7-N-diaminomethylenecarbamoyl-3,3,4,6-tetramethyl-3,4-dihydro-2H-1,4-benzothiazine-1,1-dioxide;
from methyl 3,3,4-trimethyl-6-ethyl-3,4-dihydro-2H-1,4-benzothiazine-7-carboxylate-1,1-dioxide
    7-N-diaminomethylenecarbamoyl-3,3,4-trimethyl-6-ethyl-3,4-dihydro-2H-1,4-benzothiazine-1,1-dioxide;
from methyl 3,3,4-trimethyl-3,4-dihydro-2H-1,4-benzothiazine-7-carboxylate-1,1-dioxide
    7-N-diaminomethylenecarbamoyl-3,3,4-trimethyl-3,4-dihydro-2H-1,4-benzothiazine-1,1-dioxide.

EXAMPLE 12

Analogously to Example 1, the following are obtained
from methyl 6-methyl-3,4-dihydro-2H-1,3-benzothiazine-7-carboxylate-1,1-dioxide
    7-N-diaminomethylenecarbamoyl-6-methyl-3,4-dihydro-2H-1,3-benzothiazine-1,1-dioxide;
from methyl 6-ethyl-3,4-dihydro-2H-1,3-benzothiazine-7-carboxylate-1,1-dioxide
    7-N-diaminomethylenecarbamoyl-6-ethyl-3,4-dihydro-2H-1,3-benzothiazine-1,1-dioxide;
from methyl 3,4-dihydro-2H-1,3-benzothiazine-7-carboxylate-1,1-dioxide
    7-N-diaminomethylenecarbamoyl-3,4-dihydro-2H-1,3-benzothiazine-1,1-dioxide;
from methyl 3,6-dimethyl-3,4-dihydro-2H-1,3-benzothiazine-7-carboxylate-1,1-dioxide
    7-N-diaminomethylenecarbamoyl-3,6-dimethyl-3,4-dihydro-2H-1,3-benzothiazine-1,1-dioxide;
from methyl 3-methyl-6-ethyl-3,4-dihydro-2H-1,3-benzothiazine-7-carboxylate-1,1-dioxide 7-N-diaminomethylenecarbamoyl-3-methyl-6-ethyl-3,4-dihydro-2H-1,3-benzothiazine-1,1-dioxide;

from methyl 3-methyl-3,4-dihydro-2H-1,3-benzothiazine-7-carboxylate-1,1-dioxide

7-N-diaminomethylenecarbamoyl-3-methyl-3,4-dihydro-2H-1,3-benzothiazine-1,1-dioxide;

from methyl 4-oxo-6-methyl-3,4-dihydro-2H-1,3-benzothiazine-7-carboxylate-1,1-dioxide 7-N-diaminomethylenecarbamoyl-4-oxo-6-methyl-3,4-dihydro-2H-1,3-benzothiazine-1,1-dioxide;

from methyl 4-oxo-6-ethyl-3,4-dihydro-2H-1,3-benzothiazine-7-carboxylate-1,1-dioxide 7-N-diaminomethylenecarbamoyl-4-oxo-6-ethyl-3,4-dihydro-2H-1,3-benzothiazine-1,1-dioxide;

from methyl 4-oxo-3,4-dihydro-2H-1,3-benzothiazine-7-carboxylate-1,1-dioxide

7-N-diaminomethylenecarbamoyl-4-oxo-3,4-dihydro-2H-1,3-benzothiazine-1,1-dioxide.

The following examples relate to pharmaceutical preparations:

Example A: Injection vials

A solution of 100 g of an active compound of the formula I and 5 g of disodium hydrogen phosphate is adjusted to pH 6.5 in 3 l of double-distilled water using 2N hydrochloric acid, sterile-filtered, filled into injection vials, lyophilized under sterile conditions and aseptically sealed. Each injection vial contains 5 mg of active compound.

Example B: Suppositories

A mixture of 20 g of an active compound of the formula I is fused with 100 g of soya lecithin and 1400 g of cocoa butter, poured into moulds and allowed to cool. Each suppository contains 20 mg of active compound.

Example C: Solution

A solution of 1 g of an active compound of the formula I, 9.38 g of $NaH_2PO_4.2H_2O$, 28.48 g of $Na_2HPO_4.12H_2O$ and 0.1 g of benzalkonium chloride in 940 ml of double-distilled water is prepared. It is adjusted to pH 6.8, made up to 1 l and sterilized by irradiation. This solution can be used in the form of eye drops.

Example D: Ointment 500 mg of an active compound of the formula I are mixed with 99.5 g of petroleum jelly under aseptic conditions.

Example E: Tablets

A mixture of 1 kg of active compound of the formula I, 4 kg of lactose, 1.2 kg of potato starch, 0.2 kg of talc and 0.1 kg of magnesium stearate is compressed in a customary manner to give tablets such that each tablet contains 10 mg of active compound.

Example F: Coated tablets

Analogously to Example E, tablets are pressed which are then coated in a customary manner with a coating of sucrose, potato starch, talc, tragacanth and colourant.

Example G: Capsules 2 kg of active compound of the formula I are filled into hard gelatin capsules in a customary manner such that each capsule contains 20 mg of the active compound.

Example H: Ampoules

A solution of 1 kg of active compound of the formula I in 60 l of double-distilled water is sterile-filtered, filled into ampoules, lyophilized under sterile conditions and aseptically sealed. Each ampoule contains 10 mg of active compound.

We claim:

1. A cyclic sulfone of formula I

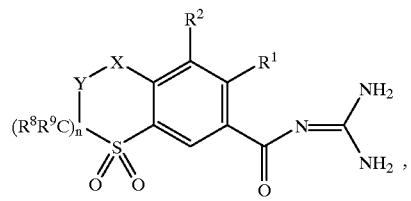

in which $R^1$ and $R^2$ in each cage independently of one another are H, A, $CF_3$, $CH_2F$, $CHF_2$, $C_2F_5$, Hal, OH, OA, $NH_2$, NHA, $NA_2$, $NO_2$ or CN, X is $CR^4R^5$, C=Z, O, S, NH, NA or $NR^3$, Y is $CR^6R^7$, C=Z, O, NH, NA or $NR^3$, Z is O, S, NH, NA, NOH, NOA, $CH_2$, CHA or $CA_2$, $R^4$, $R^5$, $R^6$ and $R^7$ in each case independently of one and another are H, A, $R^3$, Hal, OH, OA, SH, SA, $NH_2$, NHA or $NA_2$ or else $R^5$ and $R^6$ or $R^7$ and $R^8$ in each case together are also a bond, it being possible in each molecule of a maximum of only one bond of this type to occur;

$R^4$ and $R^5$ together are also O—$(CH_2)_2$—O or O—$(CH_2)_3$—O, $R^8$ and $R^9$ in each case independently of one another are H and A, A is alkyl having 1 to 6 C atoms, Hal is F, Cl, Br or I and $R^3$ is phenyl or benzyl which is unsubstituted or mono-, di- or trisubstituted by A, OA, $NH_2$, NHA, $NA_2$, F, Cl, Br and/or $CF_3$ and n is 0 or 1, or a physiologically acceptable salt thereof.

2. (a) N-diaminomethylene-2,3-dihydro-3-hydroxy-1-benzothiophene-6-carboxamide-1,1-dioxide;

(b) N-diaminomethylene-2,3-dihydro-3-hydroxy-5-methyl-1-benzothiophene-6-carboxamide-1,1-dioxide;

(c) N-diaminomethylene-2,3-dihydro-3-hydroxy-3,5-dimethyl-1-benzothiophene-6-carboxamide-1,1-dioxide;

(d) N-diaminomethylene-2,3-dihydro-3-methoxy-3,5-dimethyl-1-benzothiophene-6-carboxamide-1,1-dioxide;

(e) N-diaminomethylene-2,3-dihydro-3,5-dimethyl-1-benzothiophene-6-carboxamide-1,1-dioxide;

(f) N-diaminomethylene-2,3-dihydro-3-hydroxy-3,5-dimethyl-1-benzothiophene-6-carboxamide-1,1-dioxide;

(g) N-diaminomethylene-2,3-dihydro-3-methoxy-3,5-dimethyl-1-benzothiophene-6-carboxamide-1,1-dioxide according to claim 1, or a physiologically acceptable salt thereof.

3. A process for the preparation of a cyclic sulfone of formula I according to claim 1, or a salt thereof comprising reacting a compound of formula II

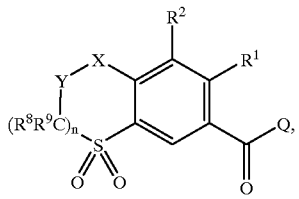

in which $R^1$, $R^2$, $R^8$, $R^9$, X, Y and n have the meanings indicated in claim 1 and Q is Cl, Br, OA, O—CO—A, O—CO—Ph, OH or another reactive esterified OH group or easily nucleophilically substitutable leaving group, with guanidine, or treating a compound otherwise corresponding to formula I, but which instead of one or more hydrogen atoms contains one or more reducible groups and/or one or more additional C—C— and/or C—N bonds, with a reducing agent, or treating a compound otherwise corresponding to formula I, but which instead of one more hydrogen atoms contains one or more solvolysable groups, with a solvolysing agent, and/or treating with an acid a base of formula I, to convert it into one of its salts.

4. A process for producing a pharmaceutical composition, comprising bringing into a suitable dose form a compound of formula I according to claim 1 and/or a physiologically acceptable salt with at least one solid, liquid or semiliquid excipient or auxiliary.

5. A pharmaceutical composition, comprising at least one compound of formula I according to claim 1 and/or physiologically acceptable salt thereof, and a pharmaceutically acceptable carrier.

6. A method of cardioprotection, comprising administering to a patient in need of such treatment an effective amount of a compound of formula I according to claim 1 or a physiologically acceptable salt thereof.

7. A method of treating or preventing arrhythmias, angina pectoris or infarcts comprising administering to a patient in need of such treatment an effective dose of a compound of formula I according to claim 1.

8. A cyclic sulfone according to claim 1, wherein

A is alkyl having 1 to 3 C atoms, $R^1$ is methyl, ethyl or H, $R^2$ is H, $R^8$ and $R^9$ are H, methyl or ethyl, and Hal is F, Cl or Br.

9. A compound according to claim 1, in the form of a racemate or an enantiomer.

* * * * *